(12) United States Patent
Hahn

(10) Patent No.: US 6,997,883 B1
(45) Date of Patent: Feb. 14, 2006

(54) DIAGNOSTIC APPARATUS FOR DETERMINING THE REMINERALIZATION ABILITY OF TISSUE

(76) Inventor: Rainer Hahn, Schwabstrasse 11, D-72074 Tübingen (DE)

( * ) Notice: Subject to any disclaimer, the term of this patent is extended or adjusted under 35 U.S.C. 154(b) by 0 days.

(21) Appl. No.: 09/402,731

(22) PCT Filed: Apr. 7, 1998

(86) PCT No.: PCT/EP98/02017

§ 371 (c)(1),
(2), (4) Date: Feb. 10, 2000

(87) PCT Pub. No.: WO98/44868

PCT Pub. Date: Oct. 15, 1998

(30) Foreign Application Priority Data

Apr. 7, 1997 (DE) ................................ 197 14 167

(51) Int. Cl.
*A61B 5/00* (2006.01)
*A61C 19/04* (2006.01)
(52) U.S. Cl. ...................................... 600/560; 600/300
(58) Field of Classification Search ................ 600/309, 600/310, 317, 322, 323, 345, 349, 361, 473, 600/476, 547, 553, 300, 560, 587, 590; 433/25, 433/27, 29, 72; 128/897; 73/38
See application file for complete search history.

(56) References Cited

U.S. PATENT DOCUMENTS

| 4,184,175 | A | * | 1/1980 | Mullane, Jr. ................. 433/29 |
| 4,215,698 | A | * | 8/1980 | Nuwayser .................... 600/547 |
| 4,479,499 | A | * | 10/1984 | Alfano ........................ 600/477 |
| 4,665,621 | A | * | 5/1987 | Ackerman et al. ............. 433/32 |
| 4,836,206 | A | * | 6/1989 | Maxwell et al. ............. 600/340 |
| 4,854,157 | A | * | 8/1989 | Wilson ......................... 73/38 |
| 4,995,403 | A | * | 2/1991 | Beckman et al. ........... 600/589 |
| 5,040,539 | A | * | 8/1991 | Schmitt et al. ............. 600/340 |
| 5,219,388 | A | * | 6/1993 | Meletiou et al. ............... 73/38 |
| 5,259,761 | A | * | 11/1993 | Schnettler et al. .......... 600/323 |
| 5,603,817 | A | * | 2/1997 | Settler et al. ................ 204/433 |
| 5,766,137 | A | * | 6/1998 | Omata ........................ 600/587 |
| 5,865,769 | A | * | 2/1999 | Case et al. .................. 600/587 |
| 6,053,731 | A | * | 4/2000 | Heckenberger .............. 433/29 |
| 6,201,880 | B1 | * | 3/2001 | Elbaum et al. ............... 433/29 |
| 6,264,470 | B1 | * | 7/2001 | Jung et al. .................... 433/29 |

FOREIGN PATENT DOCUMENTS

WO   WO 95/04506   *   2/1995
WO   WO 95/22938   *   8/1995

* cited by examiner

Primary Examiner—Eric F. Winakur

(57) ABSTRACT

The invention relates to a diagnostic apparatus with which diseased hard tissue, in particular carious dental tissue, can be examined through a small working channel, to see whether it can be made healthy again by remineralization. This diagnosis apparatus tightly (54) seals the working channel, produced in the tissue, from its environment, and places the cavity in the tissue under pressure, after which the pressurization is ended and a pressure drop is measured by means of a pressure measuring instrument (60). The speed of the drop in pressure is a measure of the extent of the changes to the diseased tissue. The invention also relates to a treatment device for supporting the remineralization or reinfiltration of diseased hard tissue and for preparing this, as well as to diagnosis and treatment agents and treatment substances.

36 Claims, 23 Drawing Sheets

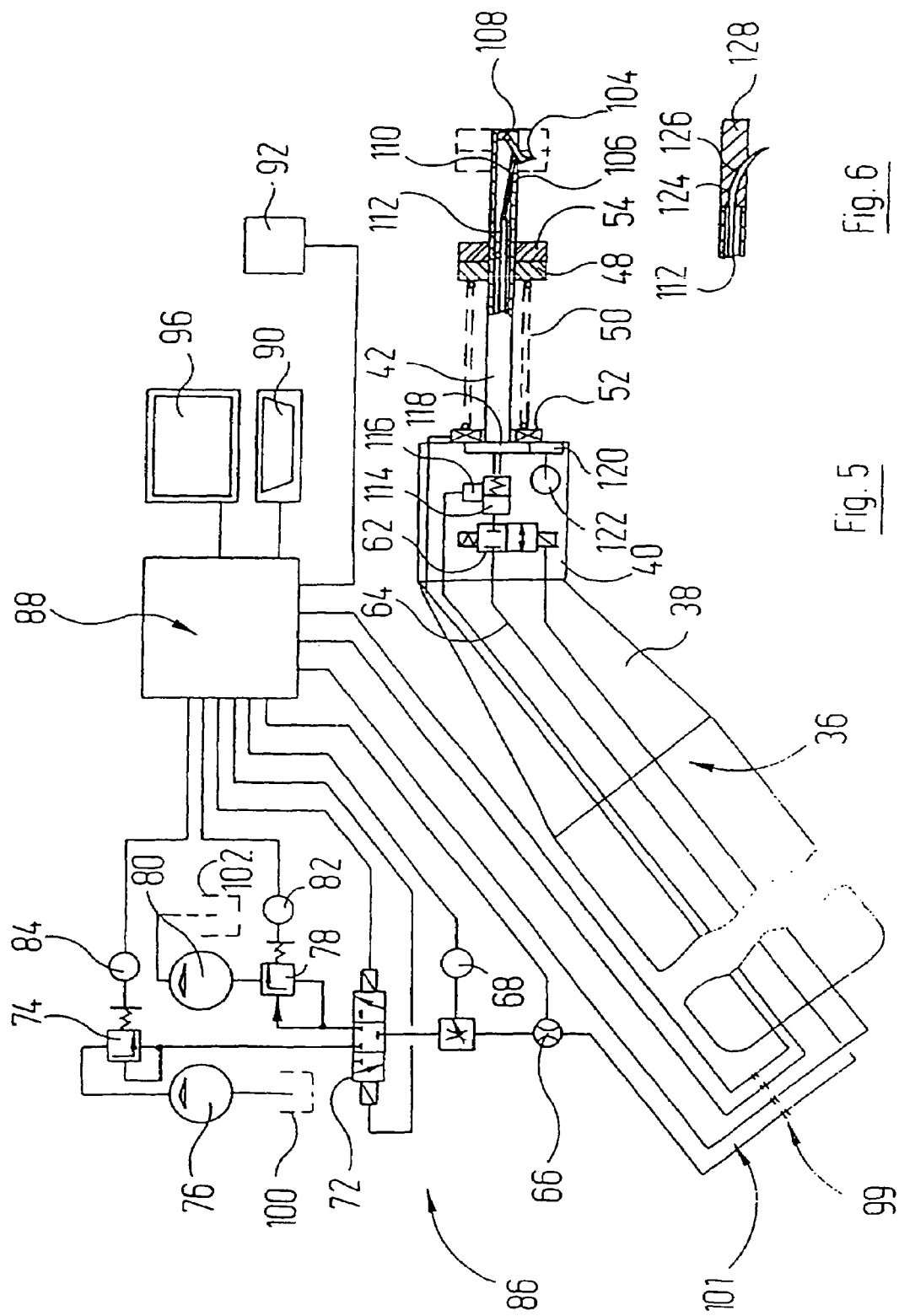

Figure 1:
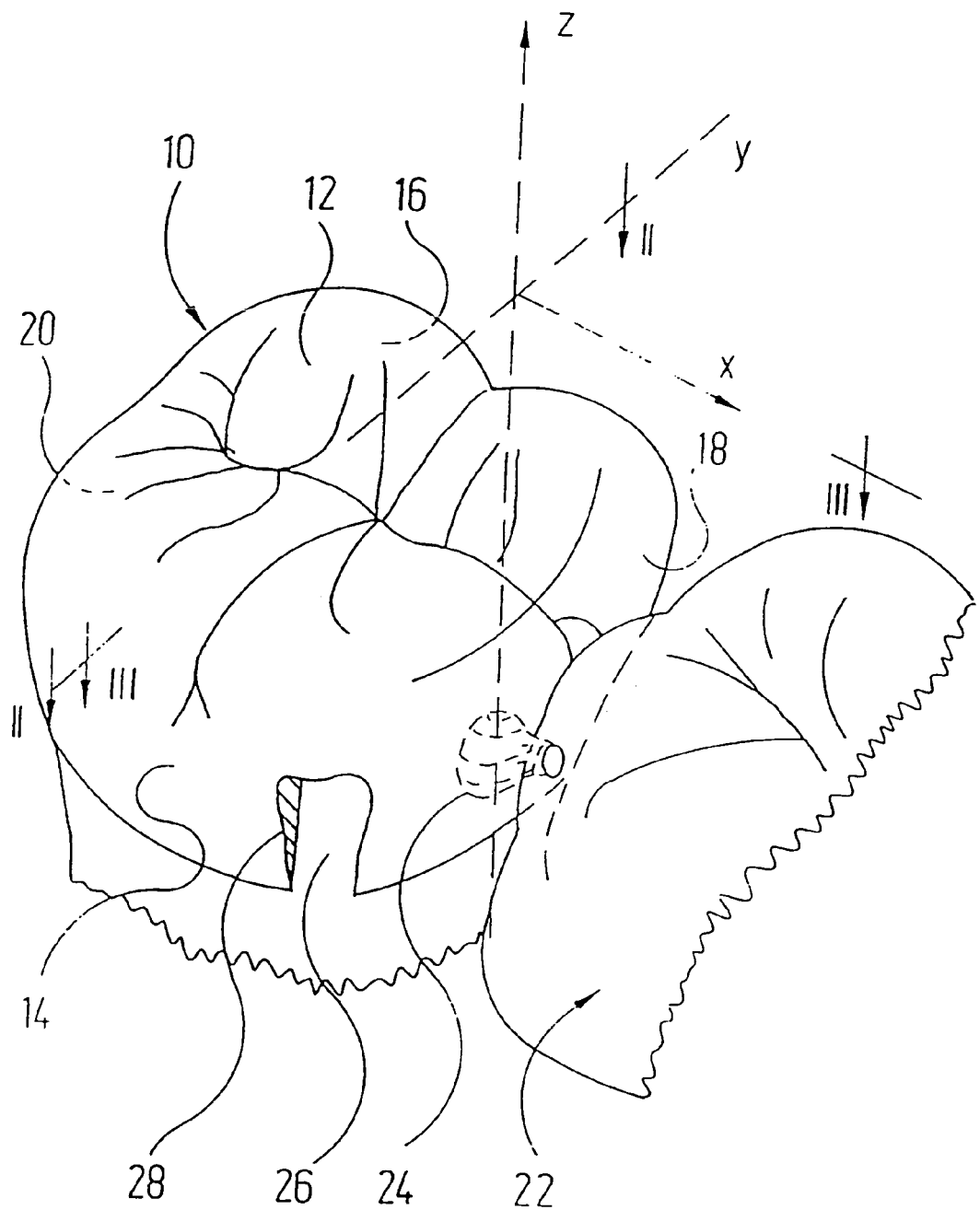

Hydrodynamic diagnosis of a suspected approximal primary caries lesion:
Inducible high pressure difference between working channel and suspected approximal caries lesion as sign of low-grade structural damage to the tooth volume region in question (end of the measurement after 18,000 ms).

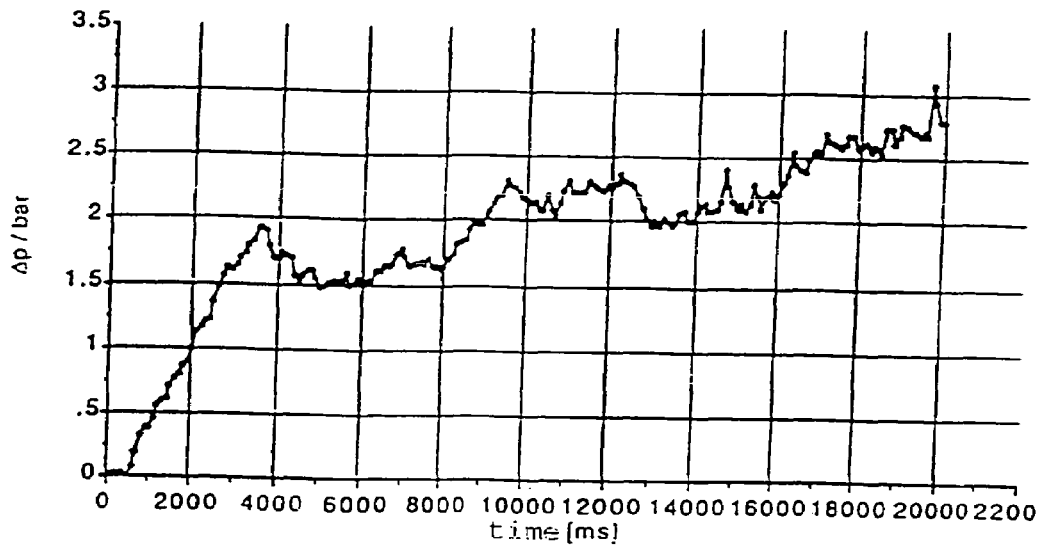

Hydrodynamic diagnosis of a suspected approximal primary caries lesion:

Inducible moderate pressure difference between working channel and suspected approximal caries lesion as sign of moderate structural damage (initial caries) to the tooth volume region in question. A suitable treatment medium is perfused into the lesion through the working channel and preferably remineralization is attempted to be induced. The success of this can be quantitatively monitored some time after this treatment in the same measuring arrangement.

Fig. 27

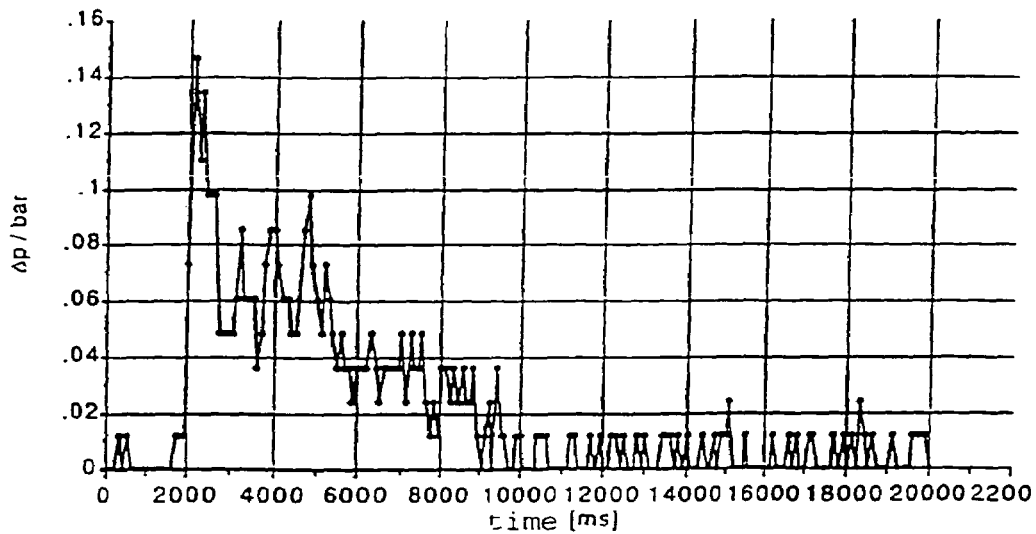

Hydrodynamic diagnosis of a suspected approximal primary caries lesion:

Despite a high volumetric flow, no pressure difference between working channel and suspected approximal caries lesion can be induced. There is incursion of the natural caries access in the sense of an open cavitation (established approximal caries); the liquid volume emerges through the natural caries access into the approximal space. Through the working channel, hydrodynamic preparation of the caries lesion is effected, the interfaces are chemically conditioned and the defect volume and the working channel are definitively closed with a suitable filling material (reinfiltrated).

Fig. 28

Hydrodynamic diagnosis of a suspected secondary caries lesion under an existing crown:

Despite a high volumetric flow, no pressure difference between working channel, crown and suspected secondary caries lesion can be induced (end of the measurement after 14,000 ms). There is incursion of the edge region of the crown in the sense of a carious cavitation. It is possible through the working channel to effect hydrodynamic preparation of the caries lesion, to chemically condition the interfaces and to definitively close (reinfiltrate) the defect volume and the working channel with a suitable filling material.

Fig. 29

Fig. 31

Outline of the process for the treatment according to the invention of approximal caries Suspected approximal caries (clinical and/or radiological)

Decision: expectant diagnosis versus microinvasive diagnosis/therapy, for example based on radiological extent ((enamel/dentine boundary not reached - dentine boundary reached - occlusal incursion))

Conv. prophylaxis — microinvasive diagnosis/induced conventional filling treatment remineralization/reinfiltration Monitoring - on progression → preparation of a tubular access (working channel) with max. Conv. prophylaxis sparing of dental hard substance (channel or tube)

Hydrodynamic and/or chemical diagnosis: Measurement and documentation of pressure gradients, amount flowing through, structure-sensitive marker substrates Caries: reversible demineralization | Caries: irreversible structural incursion Endoscop. video inspection | Hydrodynamic and/or chemical, where appropriate mechanically assisted defect preparation through the abovementioned access Where appropriate tubular closure of the working channel | Endoscop. video inspection Working channel = access for disinfection, therapeutics, monitoring | Conditioning of the defect surfaces (priming)

Reversible, bacteria-tight closure of the working channel or tube | Reinfiltration of organic structures of the defect for example with hydrophilic synthetic materials (bridging)

Monitoring, conv. prophylaxis

Possibly definitive closure of the working channel or of the tubular access in the form of fileing Refilling of the defect, for example with polymer composite (refilling)

Closure of the access cavity

DIAGNOSTIC APPARATUS FOR DETERMINING THE REMINERALIZATION ABILITY OF TISSUE

The invention relates in general to the remineralization of hard tissue, in particular carious dental tissue. For this purpose it provides on the one hand an apparatus which is able to measure the remineralization ability of such hard tissue. Also indicated is an apparatus with which the remineralization of hard tissue which has been identified as capable of remineralization can take place or be assisted. There is further indicated an apparatus with which hard tissue which has been identified as not capable of remineralization can be reinfiltrated or cavitations associated with this tissue can be filled. The invention further relates to an apparatus with which a working channel leading from the outside of the tissue to the tissue volume of interest can be produced in hard tissue which is to be investigated for its remineralization ability or is to be remineralized. Also indicated is an apparatus with which carious dental hard tissue can be removed micromechanically through the working channel. Finally, the invention relates to various media which are used in conjunction with the diagnostic apparatus or the treatment apparatus.

When hard tissue (mention is made hereinafter representatively of dental tissue in some cases) has defective areas (lesions) located on the surface of the tissue, it is usually possible to make a diagnosis by visual and tactile (scratching with a point) means.

Radiographs provide only clues to tissue defects not located on the surface. Since they reflect only generally the absorption of X-rays, but it remains unclear what proportions of the absorption is [sic] attributable to differences in tissue consistency and to tooth geometry present even in the healthy state, it is possible only with difficulty to estimate the severity and extent of such lesions. As a rule, therefore, it is necessary to create a relatively large access to such hidden lesions, through which conventional management of the lesion then takes place, namely ablation of all diseased tissue and refilling of the cavity produced in this way with plastic filling material and/or a restoration part.

With this procedure it is frequently necessary to remove considerable volumes of healthy tissue. Moreover, part of the lesions opened in this way is not irreversibly damaged and might, on the contrary, be healed by remineralization.

The present invention therefore deals generally with the problems of establishing, with very substantial retention of healthy tissue in the neighborhood of a lesion, how far the tissue lesion can be treated by remineralization and, where appropriate, of carrying out such a treatment.

For this purpose the invention provides on the one hand an apparatus for determining the remineralization ability of hard tissue, in particular carious dental tissue, which has the features indicated in Claim 1.

The invention further provides an apparatus for the remineralization and/or reinfiltration of hard tissue, in particular carious dental tissue, which has the features stated in Claim 34.

The invention further indicates an apparatus with which working channels having a small diameter can be produced from the outer surface of the tissue to the suspected defect. An apparatus of this type has the features indicated in Claim 46.

It is possible with an apparatus according to Claim 52, starting from a working channel, to remove mechanically tissue regions which can no longer be healed by remineralization, in order subsequently to carry out a reinfiltration of these regions with a settable or resettable material without the need to produce an access with a large diameter to the lesion.

The diagnostic apparatus indicated in Claim 1 measures at least one of a plurality of different physical, chemical or biological properties of the hard tissue or of the hard tissue with a carious lesion. Differences from the corresponding properties of the healthy tissue are in this case used as a measure of the severity of the lesion. Tissue properties are intended to mean in the claims and the present description both volume properties and surface properties.

These differences can in many cases be intensified by introducing through the diagnostic apparatus a marker substance whose ab- or adsorption by diseased tissue regions is different (stronger or weaker) than by healthy tissue regions. These marker substances are selected taking account of the property measured in each case, as indicated in Claim 59.

The tissue property which is primarily measured is the permeability of the tissue for liquids, in particular aqueous solutions. A better quality of diffusion barrier formed by the tissue means the presence of less tissue damage. The permeability of hard tissue for aqueous solutions is a direct measure of a remineralization ability of the tissue, since the remineralization takes place in exactly the same way as also used for the measurement.

Remineralization is possible for carious volumes where the tooth structure or dentine structure and enamel structure of the carious volume is still substantially intact but its mineral content is reduced in relation to comparable "healthy" dental hard tissue. In the case of natural remineralization, the minerals for a remineralization originate from the saliva. The remineralization returns the hard tissue to a state to be regarded as substantially healthy (restitutio ad integrum).

Remineralization is no longer possible in the case of hard tissues with more severe damage, because of structural incursions (usually localized). To treat such carious volumes (where appropriate in addition to adjacent tissue volumes capable of remineralization per se) they must, after previous conditioning or etching, be filled with a synthetic material which restores the mechanical strength and is a hindrance to further development of caries. This filling of the structural incursions takes place by infiltrating a synthetic material, a polymer or polymer composite into the diseased tooth structure which can no longer be remineralized. Since this synthetic material replaces tissue components present in the healthy tooth structure, the term reinfiltration is used.

If the monitored property of the hard tissue is, for example, its color, the marker substance can contain a coloring agent (compare Claim 60). If the monitored property is the electrical conductivity of the tissue, the marker substance can contain an electrolyte etc. As a rule, a diagnostic medium of this type is absorbed more by diseased tissue regions, because of its greater porosity or the metabolic activities of bacteria present therein, than by healthy tissue.

A treatment medium as indicated in Claim 61 serves to destroy microbes in the diseased tissue.

A treatment medium according to Claim 62 serves to open the tissue. On the one hand, this makes it possible to distinguish better between healthy and diseased tissue regions and, at the same time, provides microanchorage sites for other treatment medium or filling material.

A treatment medium according to Claim 63 comprises a primer.

A treatment medium according to Claim 64 serves to dissolve demineralized organic tissue residues.

A treatment medium according to Claim 66 allows tissue structures with severe mechanical damage, or cavities obtained by removal of diseased tissue volumes, to be filled with a filling material.

Partial mechanical closure of the pores is obtained in the case of diseased tissue with large pores using a treatment medium according to Claim 67. In the diagnosis phase it is possible by successive use of treatment media with increasingly large particle size and, in parallel with this, monitoring of the fluid leakage through the diseased tissue regions to draw further conclusions about the extent of the tissue damage.

The use of a treatment medium according to Claim 70 makes it possible also to provide a treatment for the pulp adjacent to or enclosed in a lesion region.

The treatment medium indicated in Claim 71 provides the element fluorine which is particularly important for remineralization.

It is possible with a treatment medium according to Claim 72 to achieve a plurality of the constituent objects mentioned above.

Packaging of media according to Claim 73 is advantageous in connection with simple application of the diagnostic and/or treatment medium. The plug connection part of the container containing the diagnostic and/or treatment medium is simply pushed into the end of a working channel produced in the tissue or pushed onto an appropriate counterpart of a treatment apparatus. The medium can be delivered in a controlled manner by deformation of the container. The plug connection part is initially closed and is cut to the length desired in each case, which simultaneously unseals and opens the storage container.

A treatment article according to Claim 74 allows long-term treatment with a treatment medium to be carried out. This procedure is particularly advantageous for introducing fluoride or chlorhexidine into diseased tissue which is to be remineralized where appropriate.

A treatment article according to Claim 77 can be used to prevent growing together and thus keep the working channel open for a prolonged period in order to carry out checks and/or treatments of a lesion at relatively large time intervals.

Advantageous further developments of the invention are indicated in dependent Claims.

The further development of the invention according to Claim 2 permits the probe section of the measuring head to be introduced with accurate fit into a working channel produced in the hard tissue, so that the mutually opposite surfaces of working channel and probe section form an aerodynamic seal.

The further development of the invention according to Claim 3 allows the intensity and extent of a diseased tissue region to be determined.

A probe position indicator as indicated in Claim 4 is distinguished by a design which is particularly mechanically simple.

The further development of the invention according to Claim 5 allows determination in a simple way of base line values of the tissue property under consideration, as found in the neighborhood of the lesion in the patient under consideration. It is then possible to detect particularly precisely pathological differences by reference to these individual and site-specific reference values.

The further development of the invention according to Claim 6 allows measurement, resolved not only in the axial direction but also in the radial direction, of tissue properties in a working channel produced in the tissue.

The further development of the invention according to Claim 7 is advantageous in relation to manipulation, which is ergonomically favorable for the dentist, of the diagnostic apparatus in diversely restricted regions of a patient's mouth.

The ergonomics of the diagnostic apparatus are also served by the further development of the invention according to Claim 8.

The further development of the invention according to Claim 9 permits unimpeded rotation of the grip part around its long axis.

The further development of the invention according Claim 10 permits investigation of the tissue property under particular consideration within wide limits.

An apparatus according to Claim 11 is particularly simple to manipulate.

The further development of the invention according to Claims 12 and 13 moreover achieves the production of negligible additional defects in the tissue by the measurement used for diagnostic purposes, which is particularly advantageous on measurement of the mechanical hardness of the tissue, where relatively extensive penetration of a test point into the tissue would necessarily be expected in the diseased tissue regions.

A diagnostic apparatus according to Claim 14 can be used to diagnose the extent and the severity of the damage to a tissue particularly gently by fluidic measurement of its porosity. As already explained above, the ability of tissue to form a diffusion barrier for fluids is a measure of the health of tissue in general. It must be taken into account in this connection that a carious disorder of teeth frequently likewise involves frequently dentine with its tubular structure and high water content, carious enamel with its relative proportions of water and organic tissue which are higher by comparison with healthy enamel, and dentine with carious lesions and likewise with relative proportions of water and organic tissue which are higher by comparison with healthy dentine. Although a measurement of permeability carried out on a specific diseased tissue region cannot resolve in detail which type of tissue is damaged to what extent, it does give overall good information about the extent and severity of the damage.

If a gas is used as measuring fluid, as indicated in Claim 15, even small tissue defects can be determined satisfactorily, and as a rule small pressure differences from the normal pressure are sufficient for the diagnosis.

The further development of the invention according to Claim 16 moreover allows differentiation of more severely damaged tissue regions because more fluid is available for a measuring procedure.

The further development of the invention according to Claim 17 is advantageous in relation to the quantitative measurement of relatively severe tissue defects.

A diagnostic apparatus according to Claim 18 can be used for very simple visual identification and measurement of leakages through defective tissue regions.

A diagnostic apparatus according to Claim 19 is of particularly compact construction and is particularly simple mechanically because the spring of the position indicator can simultaneously serve as pretensioning spring for the sealing element.

A diagnostic apparatus according to Claim 20 can determine the tissue properties with axial and radial resolution in the tissue regions surrounding a working channel.

The further development of the invention according to Claim 21 is advantageous in relation to a particularly effective sealing of the working channel toward the environment because there is an extensive good sealing area between the outer surface of the probe section and the inner surface of the tubular sealing element, but especially also between the flared end of the sealing element and the sealing connection of the probe section.

The further development of the invention according to Claim 22 measures the fluid exchange between tissue and measuring probe. It is possible in this way to establish the condition of tissues which are located further inside a tissue, as well as in the case of lesions which have not yet led to fluid leakages to the surface of the tissue.

A diagnostic apparatus according to Claim 24 operates mechanically; the results obtained with it are directly comparable to those obtained with the known probes placed on the tooth surface.

The further development of the invention according to Claim 25 allows the measuring probe to be moved unimpeded with retracted measuring point in a working channel produced in the tissue, it being possible to measure the tissue characteristics at selected sites in this working channel by advancing the measuring tip.

In this connection, the measuring tip mechanism indicated in Claim 26 is distinguished by a design which is particularly simple mechanically and reliable.

The further development of the invention according to Claim 27 moreover allows adjustment of the force exerted by the measuring point on the tissue. A diagnostic apparatus of this type is suitable for the type of measurement already indicated above with reference to Claim 13, in which the force required to bring about a preset depth of penetration of the measuring point is measured.

In a diagnostic apparatus according to Claim 28, the tissue investigation is carried out with light, in which case the image of the tissue surface generated by the image converter allows differentiation between healthy and diseased tissue on the basis of the surface structure and, where appropriate, the surface color or different intrinsic fluorescence effects.

With a diagnostic apparatus according to Claim 29, the differentiation between diseased and healthy tissue is based on the color or the fluorescence, it being possible to enhance the contrast by using a diagnostic medium which is absorbed to different extents by diseased and healthy tissue and contains a coloring agent (compare Claim 59).

A diagnostic apparatus according to Claim 30 makes use of the fact that the absorption and/or damping of mechanical vibrations by diseased tissue differs, because of its more porous structure, from that by healthy tissue. This results in a different mechanical load for a vibrator cooperating with the tissue, which load can be detected on the generator feeding the vibrator. The vibrator may be a mechanical vibrator which interacts directly with the tissue surface, or an acoustic or ultrasonic vibrator which may also vibrate at a small distance from the tissue surface.

According to Claim 31, the difference in response of healthy and diseased tissue to mechanical vibrations can be measured by operating a vibrator and a receiver with a timeshift so that the receiver records the vibrations reflected by the tissue.

It is also possible, according to Claim 32, to determine in a non-tissue-damaging manner the extent of tissue damage via the local electrical conductivity and/or change in impedance (on use of alternating current) and/or a frequency shift.

Production of a working channel extending through healthy and diseased tissue regions leaves on the tissue surface small fragments of tissue which have been forced into the tissue surface by the drilling tool. It is possible with a diagnostic apparatus according to Claim 33 for these to be transferred into a test tube, it being possible at the same time for some liquid also to be sucked out of the pores of the tissue. After removal of the test tube, the various surface sections thereof can be investigated for such tissue particles and aspirated tissue fluid. This also provides an image with axial and radial resolution of diseased tissue regions.

A treatment apparatus according to Claim 34 makes it possible to supply treatment medium forcibly to the diseased tissue. This results in a vigorous exchange of medium between tissue and treatment apparatus, by which means the pores or cavities of the tissue are intensively filled with the treatment medium, or the water content in the tissue is perfused with active substances. This apparatus can also be used to supply different treatment media successively to the tissue.

A treatment apparatus according to Claim 35 permits fluid to be aspirated out of the diseased tissue, which makes it possible for the latter subsequently to absorb a diagnostic or treatment medium better.

A treatment apparatus according to Claim 36 is particularly suitable in connection with diseased tissue regions which have been made accessible via a drilled working channel.

It is possible with a treatment apparatus according to Claim 37 to carry out the tissue treatment with different intensities in the axial direction and in the radial direction of the operating channel, that is to say to supply the treatment media specifically only to the diseased tissue regions.

Such a specifically different axial treatment of tissue is facilitated by a treatment apparatus through Claim 38. It is possible with it to establish the actual axial position of the delivery section of the working head reliably and accurately. The axial position indicator provided for this purpose has a mechanically simple design.

In a treatment apparatus according to Claim 39, the spring of the axial position indicator simultaneously serves as pretensioning spring for a sealing means by which the delivery section of the working head can be sealed against the tissue surface.

The further development of the invention according to Claim 40 serves to make the dentist's mode of operating ergonomically favorable and permits the treatment even of areas of the teeth which are difficult to access.

The further developments of the invention according to Claims 41 to 43 also serve to make manipulation of the treatment apparatus simple and convenient.

Some of the treatment media used for remineralization of diseased hard tissue are relatively costly. Moreover, it is often desired to use several such treatment media successively. In connection with this, it is advantageous if the source of the treatment medium is as close as possible to the delivery section of the working head. A corresponding further development of the in invention is indicated in Claim 44.

If tissue regions to be remineralized are located close to the tooth surface so that a fluid-tight barrier layer to the outside of the teeth no longer exists, it is possible with low-viscosity treatment media for these to penetrate through to the outside of the teeth. With the further development of the invention according to Claim 45 there is controlled removal of such emerging portions of treatment media so that they do not get into the mouth of the patient or onto adjacent tooth surfaces. It is possible in this way for the treatment apparatus to carry out a vigorous exchange between liquid which is initially present in the defect volume and liquid supplied through the treatment apparatus.

The further development of the invention according to Claim 47 makes it simple to lead a working channel which is to extend from the outside of the tooth to the diseased tissue region to the exact distance into the interior of the tissue necessary according to the location of the diseased tissue region which has previously been roughly established.

Diameters of the drilling tool indicated in Claim 48 on the one hand represent an adequate access to the diseased tissue region but remove only a small amount of healthy tissue.

If a hollow drilling tool as indicated in Claim 49 is chosen to produce the working channel, the drilled core present in the inside of the drilling tool can be pushed out of the drilling tool with a thin wire and be investigated for its property with axial resolution. The diseased tissue region can also be localized more accurately in this way.

The further development of the invention according to Claim 50 allows a working channel having a small diameter to be produced gently and efficiently without severe damage to the adjacent tissue.

The further development of the invention according to Claim 51 is moreover advantageous in relation to an improvement of the ablation efficiency. If only abrasive particles having a small diameter are added to the abrasive liquid, it is possible for those abrasive particles forced permanently into the cut tissue regions by ultrasound simultaneously to serve as seal and adherent surface.

It is moreover possible with a cutting tool as indicated in Claim 53 to undertake removals projected back further radially from the working channel.

The further development of the invention according to Claim 54 is advantageous in relation to the outside of the cutting tool having a smooth surface in the resting configuration used for insertion.

In an apparatus according to Claim 54, the adjustable cutting tool represents in the resting configuration a partial continuation of the tool shaft.

The further development of the invention according to Claim 55 is advantageous in relation to an increased cutting efficiency.

An apparatus according to Claim 56 has a cutting tool which is distinguished by a design which is mechanically particularly simple. The cutting edge of such a tool can also be adjusted particularly precisely in the radial direction.

With an apparatus according to Claim 57, the radially adjustable cutting edge is, or the radially adjustable cutting edges are, in contact under elastic pressure with the tissue to be cut out. This results in preferential removal of diseased tissue regions, while there is less extensive ablation of healthy tissue regions.

The further development of the invention according to Claim 58 results in a very large number of cutting edges which are adjustable in the radial direction.

The further development of the invention according to Claim 60 makes improved visual identification of diseased tissue regions possible.

Claims 61–63 relate to preferred treatment media for carious dental hard tissue.

The further development of the invention according to Claim 64 allows the removal of organic tissue residues which would impede subsequent remineralization or reinfiltration.

The concentration data indicated in Claim 65 for the substance dissolving organic tissue residues have proved particularly suitable in practice in relation to, on the one hand, reliably dissolving organic residues out of the hard tissue and, on the other hand, not attacking the latter to an unreasonably large extent.

The particulate components indicated in Claim 68 for the treatment medium can be used on the one hand for ablation of material which can no longer be remineralized. In this case, the treatment medium is a suspension of such particles, and a tool powered by high frequency sound, in particular ultrasound, is used to ablate the severely damaged tissue volume, with the cavitation effects produced by ultrasound being assisted by the abrasive properties of the particles. The particles indicated in Claim 68 can, however, also be introduced previously into the defect volumes or be added to the material to be reinfiltrated, so that they represent filling particles in the reinfiltrated defect volumes. However, particles of this type can also in addition be used for diagnostic purposes, for example for radiological marking of a defect volume.

In this connection, the particle sizes indicated in Claim 69 have proved particularly suitable in practice.

If the particles are used to assist ablation of tissue, the particle size is <100 $\mu$m, preferably <50 $\mu$m, again preferably <20 $\mu$m and particularly preferably <10 $\mu$m. If the particles are to be filling particles, the preferred particle size is <50 $\mu$m, again preferably <20 $\mu$m, once again preferably <5 $\mu$m and very particularly preferably <2 $\mu$m.

Treatment of the pulp is possible with a treatment medium according to Claim 70.

A treatment medium according to Claim 71 is advantageous in relation to supply of substances assisting remineralization, such as fluorine, to defective tissue volumes.

The further development of the invention according to Claim 72 makes it possible to pack a plurality of chemical types of treatment of the diseased tissue in one treatment step. This shortens the treatment time.

The further development of the invention according to Claim 73 allows packaging of diagnostic or treatment media in the factory in amounts appropriate for a single use in each case. Delivery of diagnostic or treatment medium can be controlled in a simple manner by the clinician, manually or by means of a motor-controlled treatment apparatus.

Appropriate deformable containers for the treatment medium can be produced very cost-effectively from injection molded synthetic material. Cutting off the connecting part makes it possible to open the container and adjust the length of the plug connection part simultaneously.

It is moreover possible, according to the further development of the invention according to Claim 75, for the basic article carrying the treatment medium to remain in the working channel for a long period or permanently. An end section, which is adjacent to the tooth surface, of the basic article, whose length approximately corresponds to the thickness of the tooth enamel cap, can be firmly connected to the opposite section of the wall area of the working channel, for example by cement, synthetic material, a compomer or a similar material. This results in closure of the working channel on the outside in the form of a provisional or definitive closure, with inclusion of the basic article.

The further development of the invention according to Claim 76 moreover permits the release of the treatment medium to be controlled in the way known per se for slow release drug products, and in the case where the treatment medium contains fluoride or chlorhexidine, the resin material is preferably chosen so that the fluoride or chlorhexidine release is distributed over some months.

With a treatment article according to Claim 77 it is possible, after removal of its closure, to obtain access once again to the diseased tissue region for further measurements or for introducing new active substances.

With a treatment article according to Claim 78, the healthy tissue parts are protected from treatment liquids which are supplied to the diseased tissue parts through the treatment article.

A treatment article according to Claim 79 results in good sealing in relation to the outer end of a working channel into which the treatment article is inserted.

A treatment article as indicated in Claim 80 does not need to be removed in a separate step after completion of the treatment of the diseased tissue region. It can remain permanently as filling article in the tooth.

Positive pressures as indicated in Claim 81 for the diagnostic apparatus allow a particularly valid conclusion to be drawn about the nature and extent of a hard tissue lesion.

The further development of the invention according to Claim 82 is advantageous in relation to a transient reduction in the viscosity of the diagnostic or treatment medium and thus in relation to a good supply of these media to the diagnostic or treatment site.

In an apparatus according to Claim 83, this viscosity reduction takes place directly in the supply part, which is only thin.

The further development of the invention according to Claim 84 makes it possible also to execute a transient reduction in its viscosity.

An apparatus according to Claim 85 further permits the drilling of a working channel using a drilling tool oscillating with the frequency of sound or ultrasound.

It is moreover possible according to Claim 86 to increase the drilling efficiency.

A diagnostic medium according to Claim 87 can be used to measure the porosity of severely damaged tissue regions by successive blocking of the large pores.

The further development of the invention according to Claim 88 permits continuous adjustment of the viscosity of the diagnostic medium and thus to measurement regions of diverse classes of damage.

Figure 2:
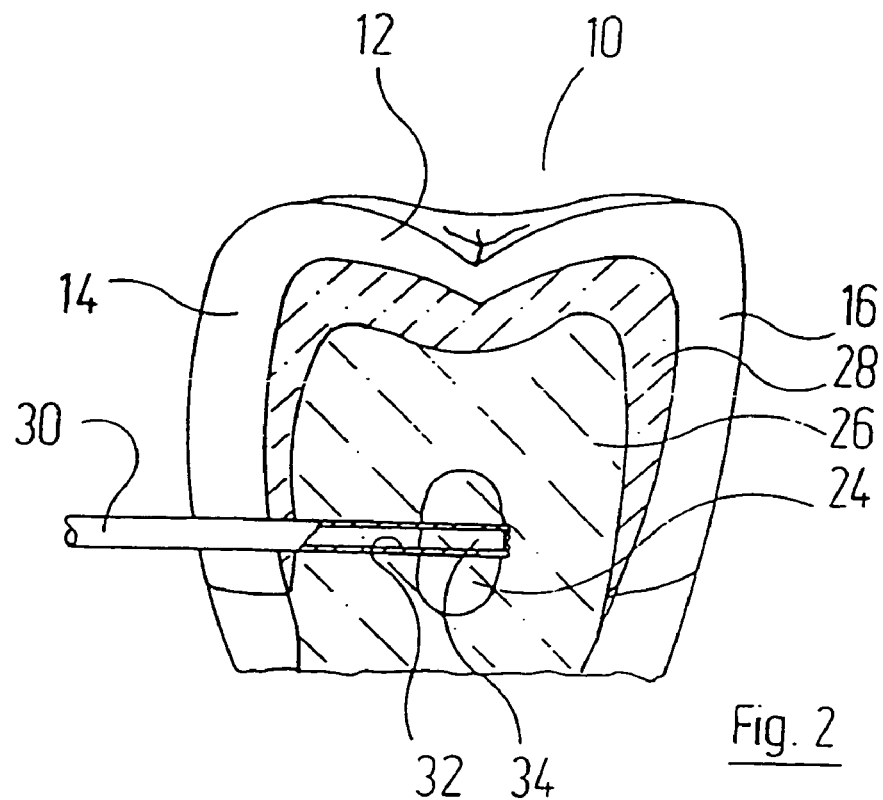
Figure 3:
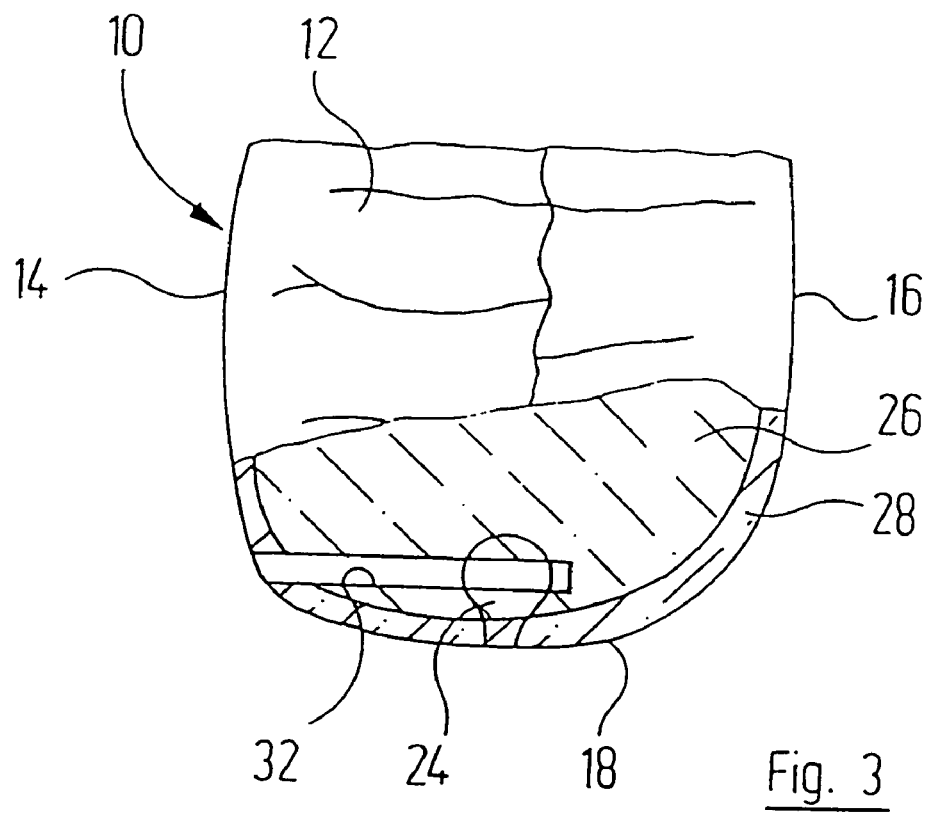
Figure 4:
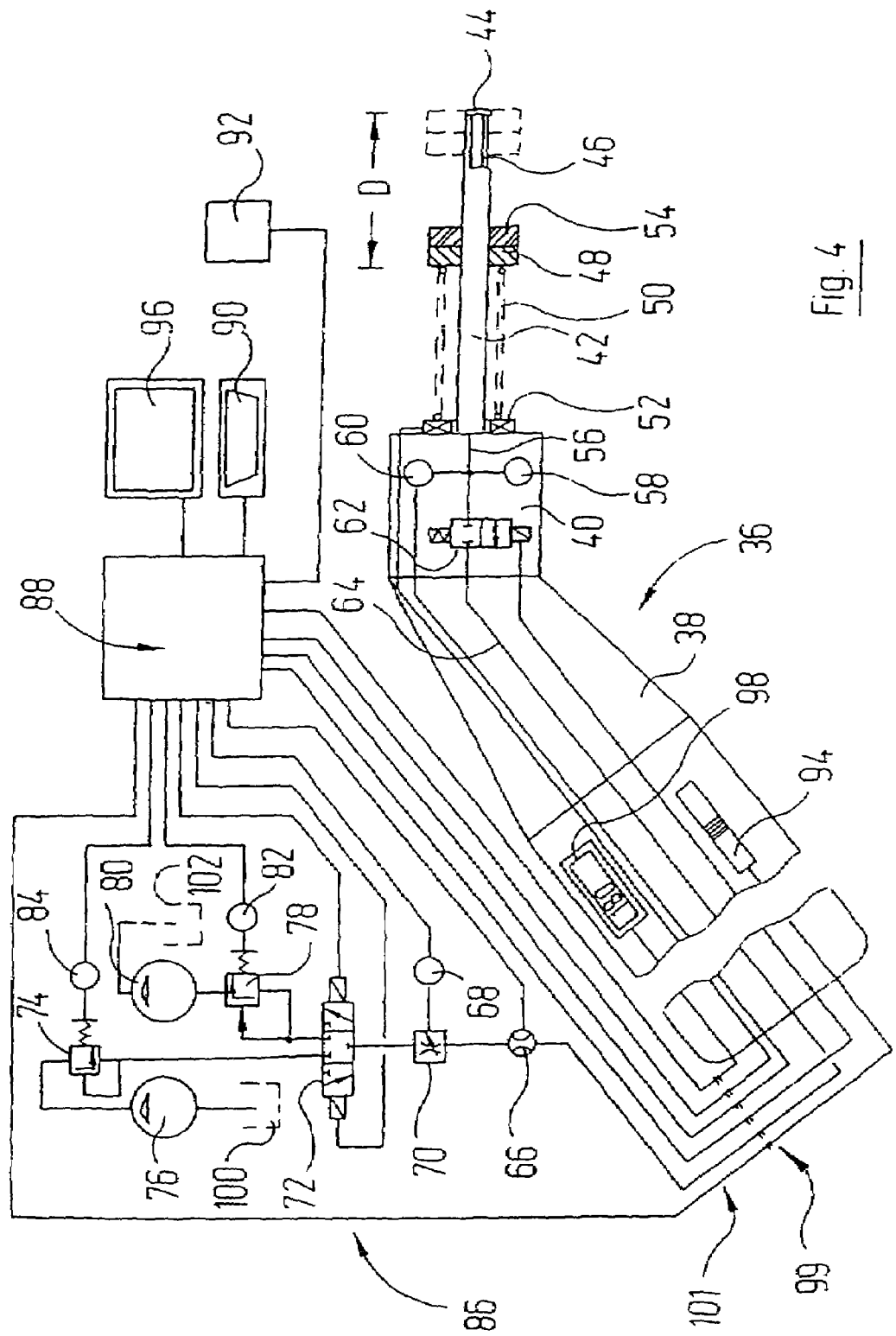

The invention is explained in more detail hereinafter by means of exemplary embodiments with reference to the appended drawing. This shows in:

FIG. 1: a perspective view of a molar tooth with a diseased tissue region adjacent to the neighboring tooth;

FIG. 2: a vertical section through the molar tooth shown in FIG. 1 along section line II—II therein;

FIG. 3: a horizontal partial section through the molar tooth shown in FIG. 1 along the section line III—III therein;

FIG. 4: a diagrammatic representation of a diagnostic and treatment apparatus for carious tissue located inside a tooth, and of an appertaining fluid supply unit and of an appertaining electronic evaluation and control unit;

FIG. 5: a similar representation as FIG. 4, in which a modified diagnostic apparatus is shown;

FIG. 6: an axial section through the end of a probe section of the diagnostic apparatus as shown in FIG. 5

Figure 11:
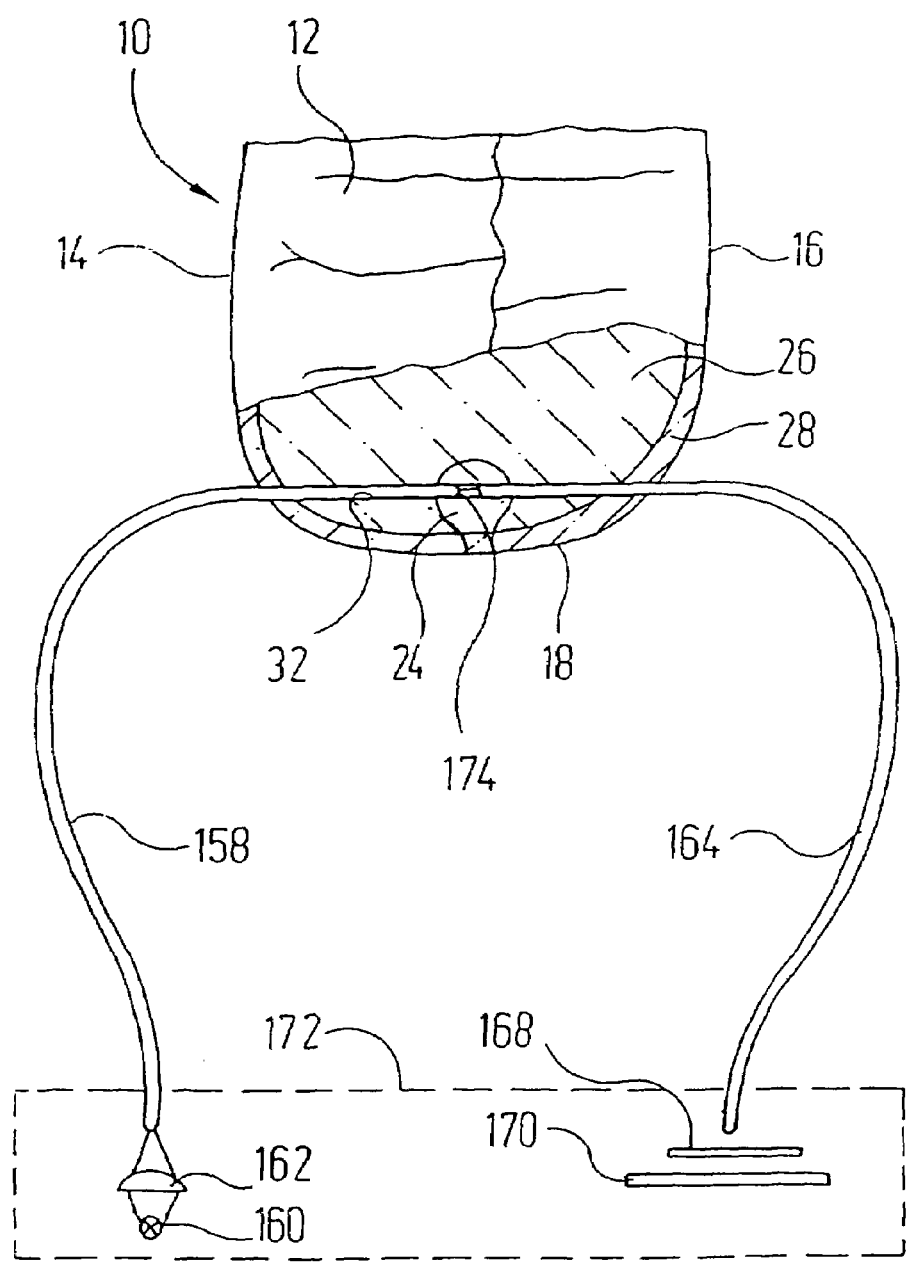
Figure 12:
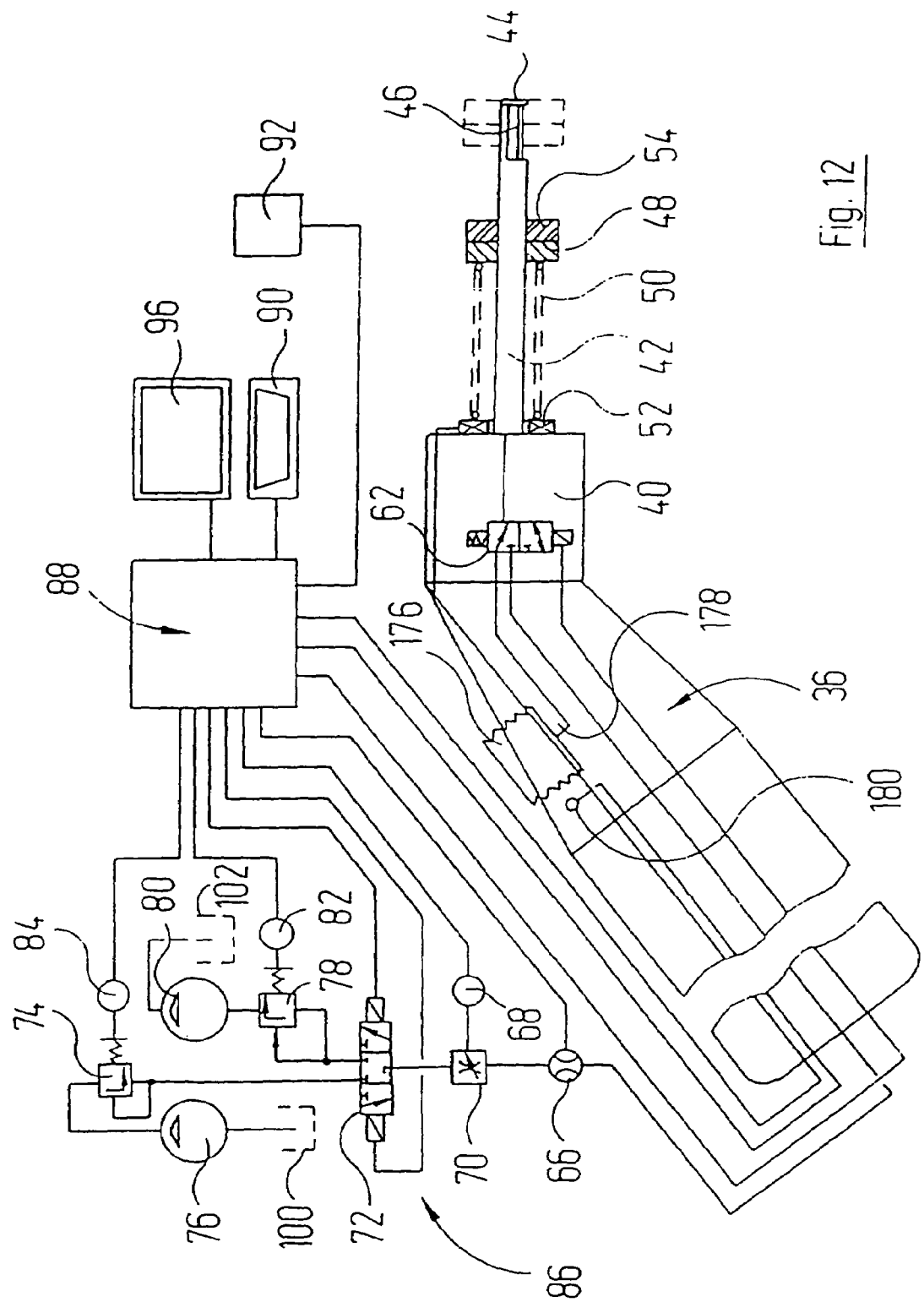
Figure 13:
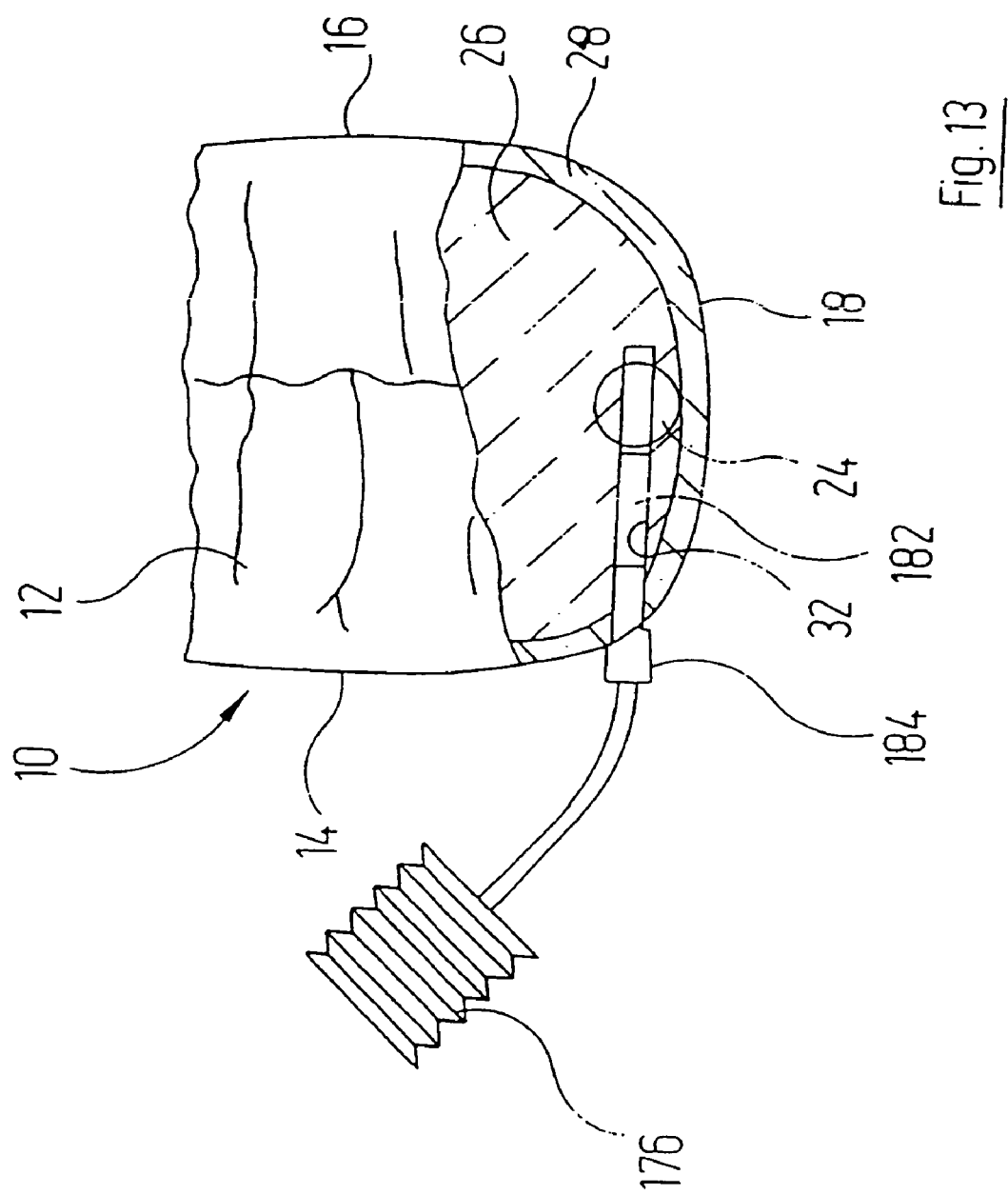
Figure 14:
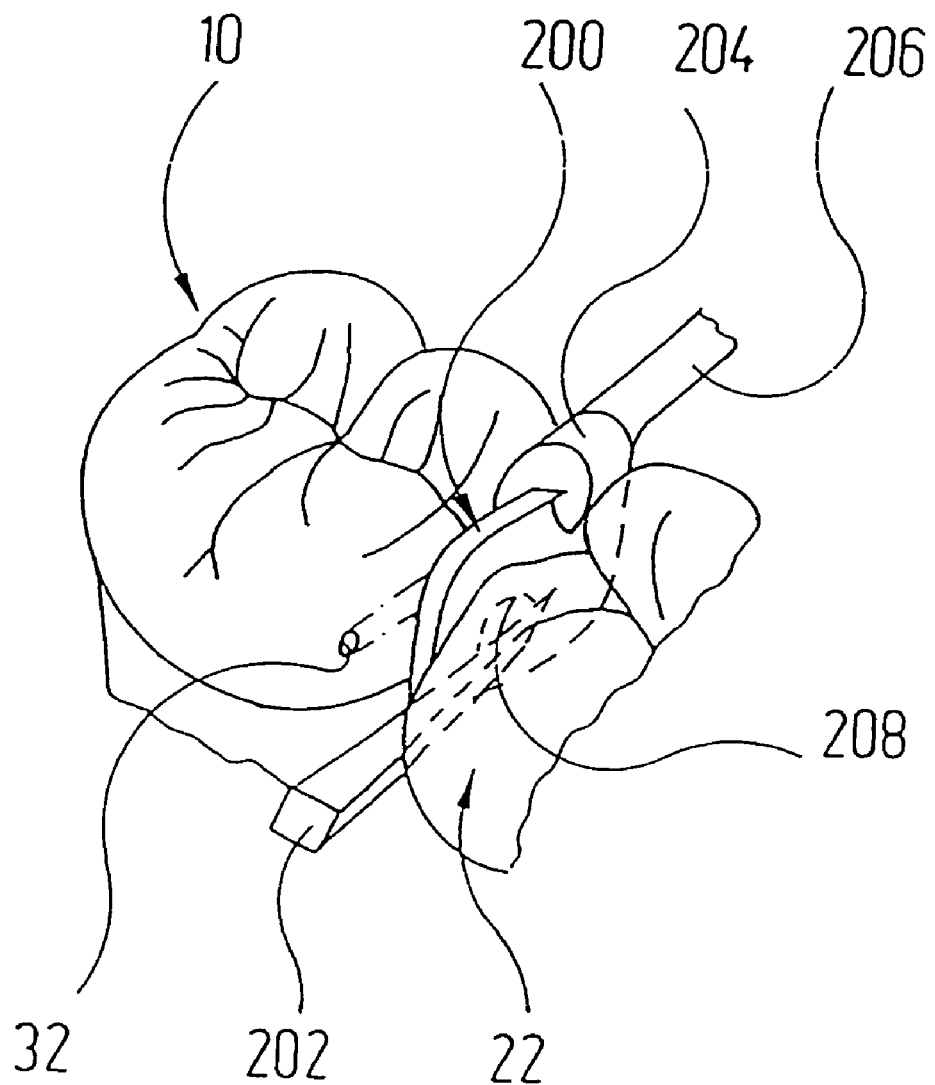
Figure 15:
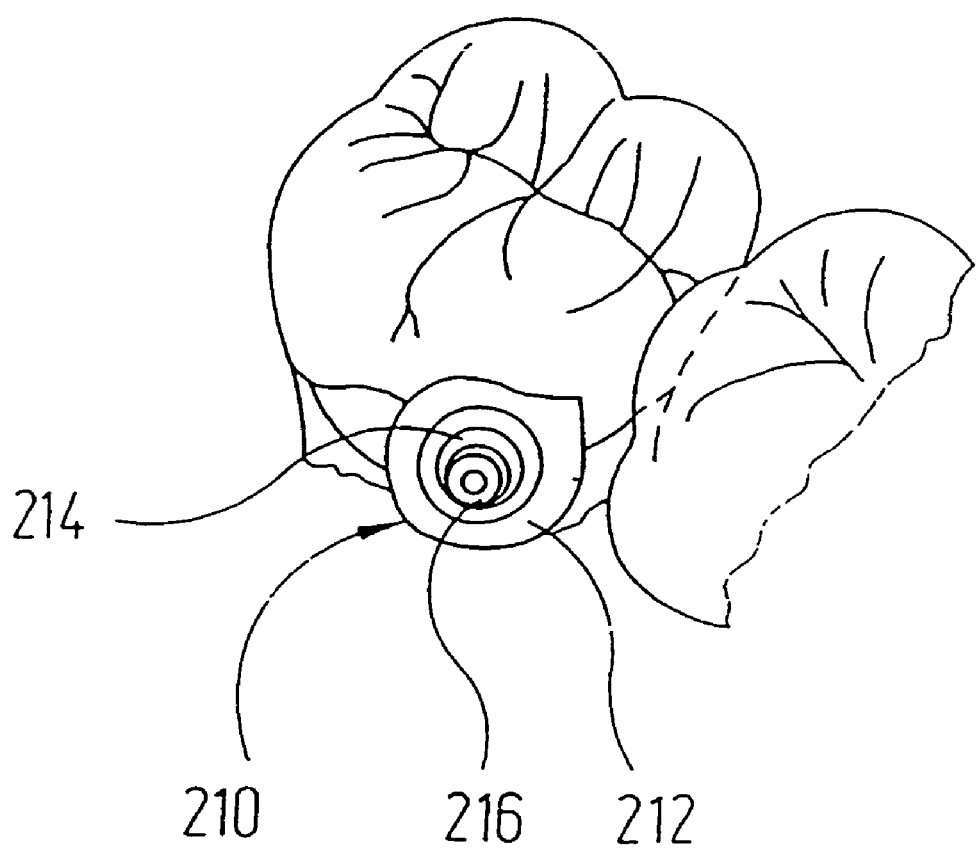
Figure 16:
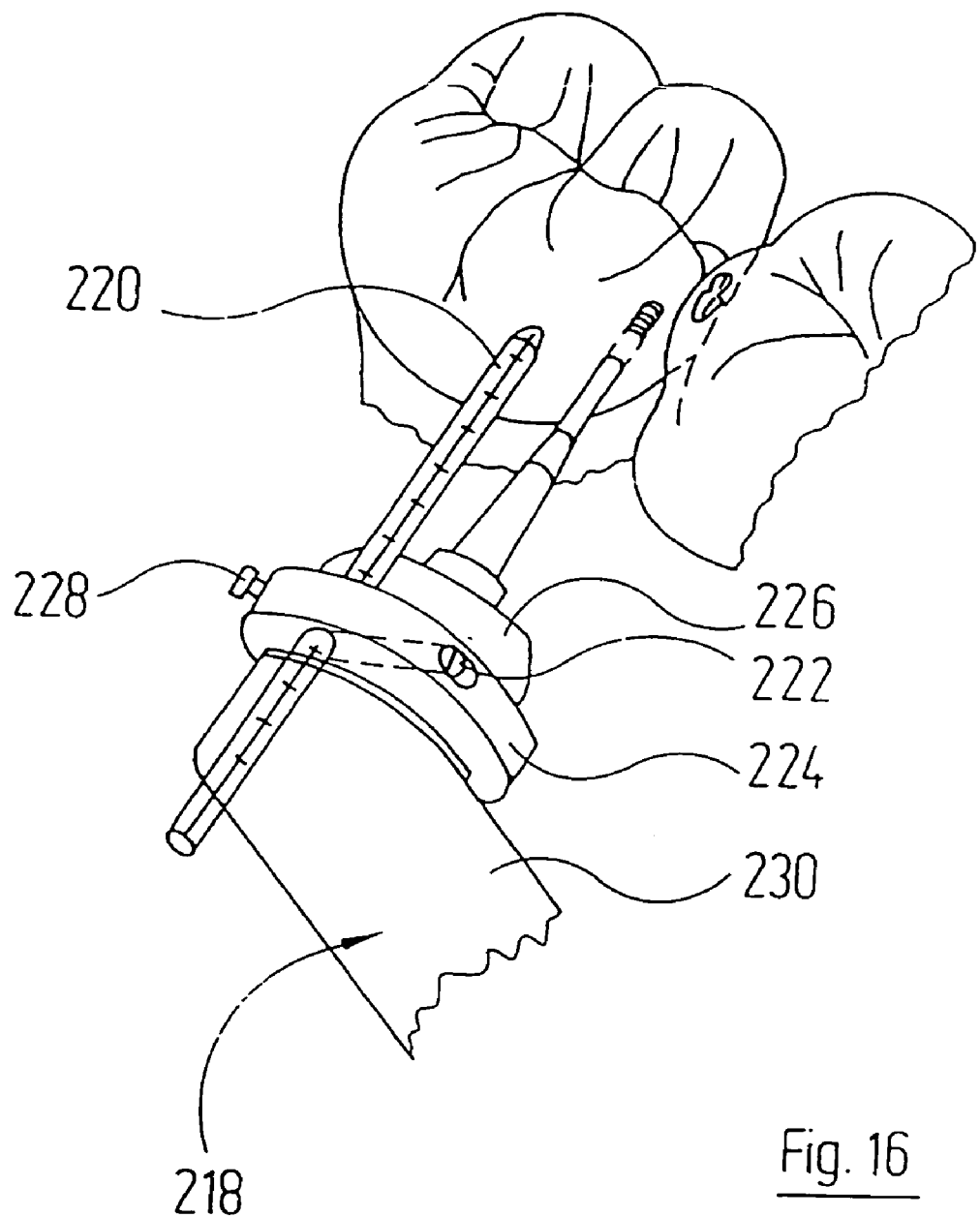
Figure 17:
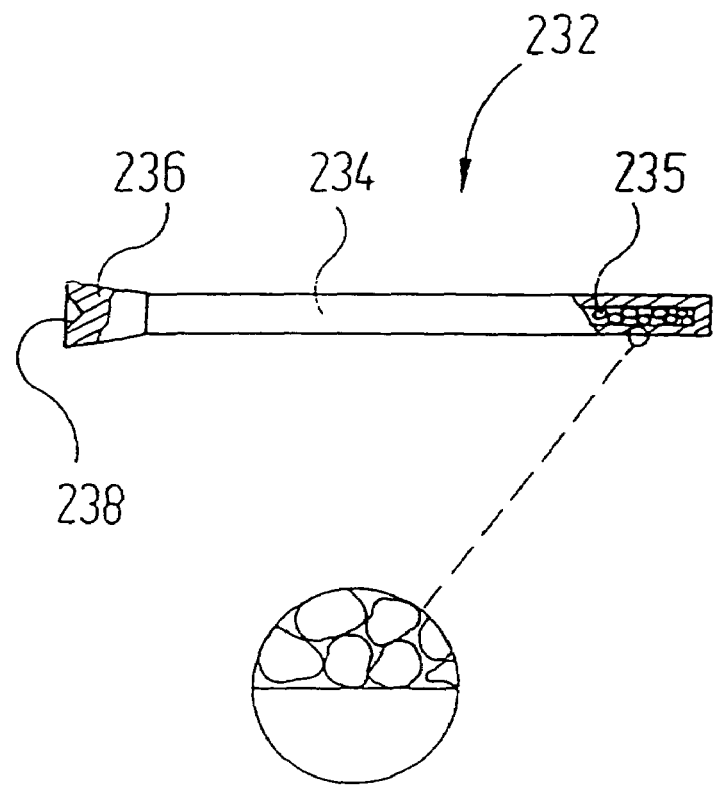
Figure 18:
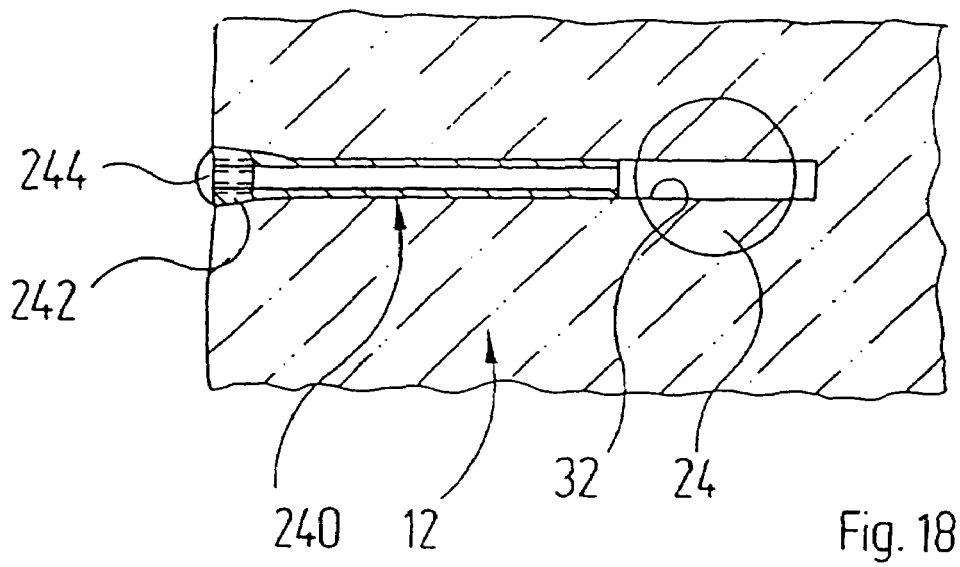
Figure 19:
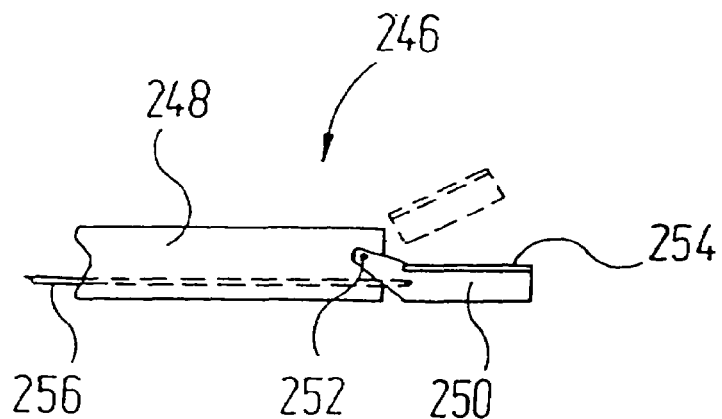
Figure 20:
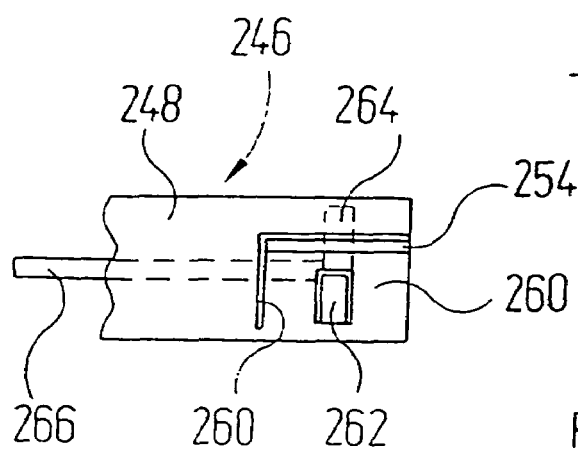
Figure 21:
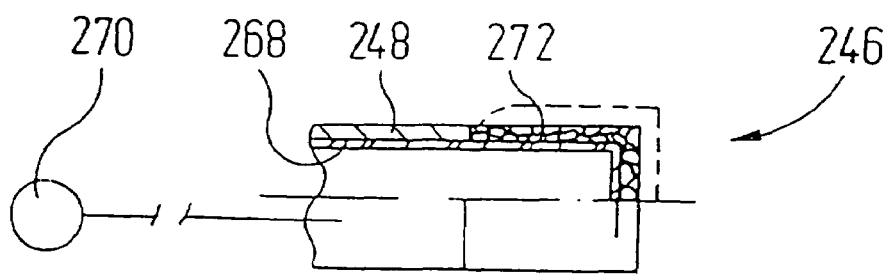
Figure 22:
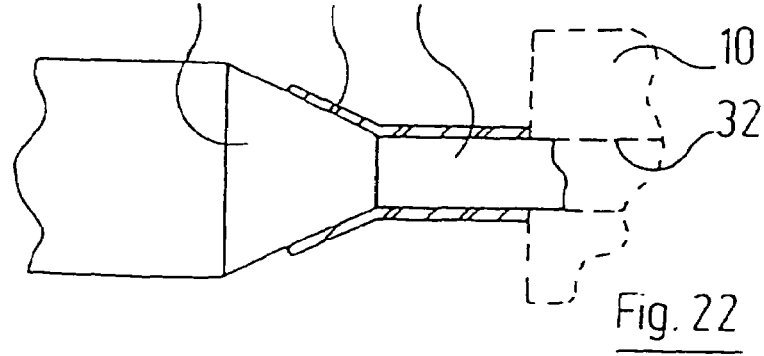
Figure 23:
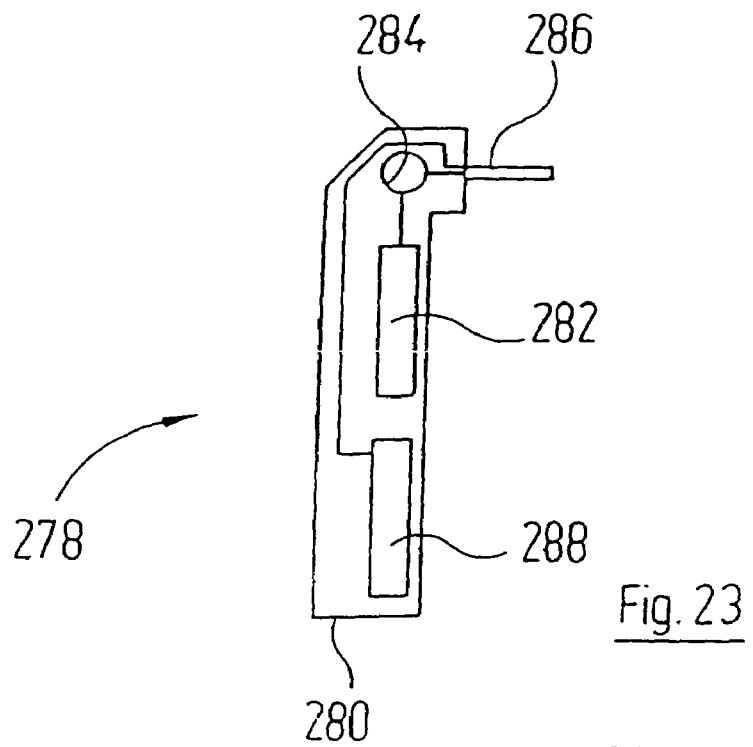
Figure 24:
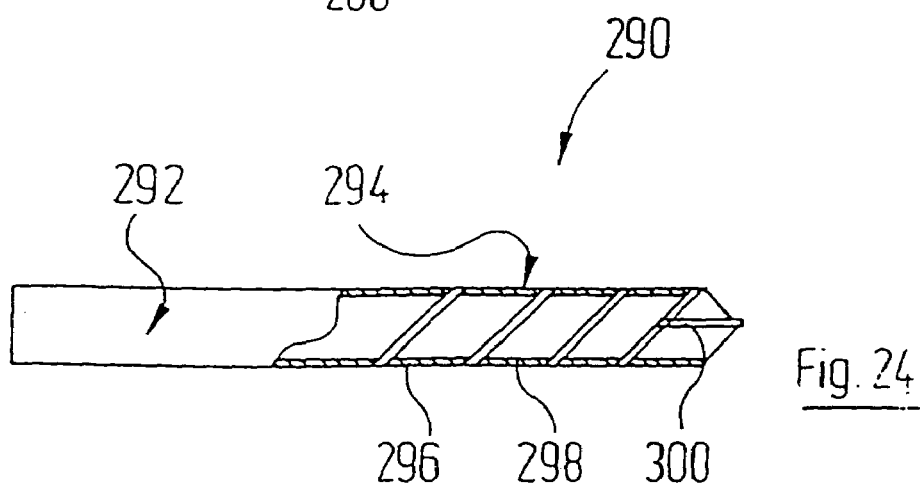
Figure 25:
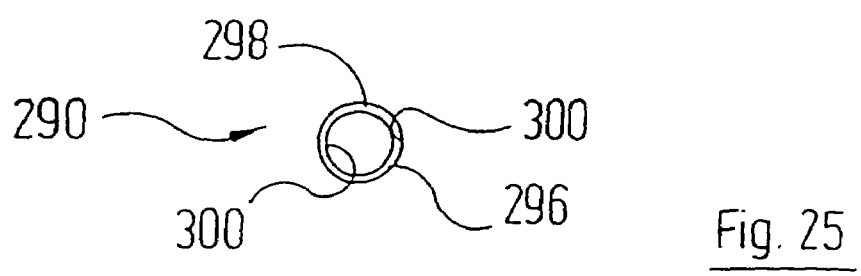
Figure 26:
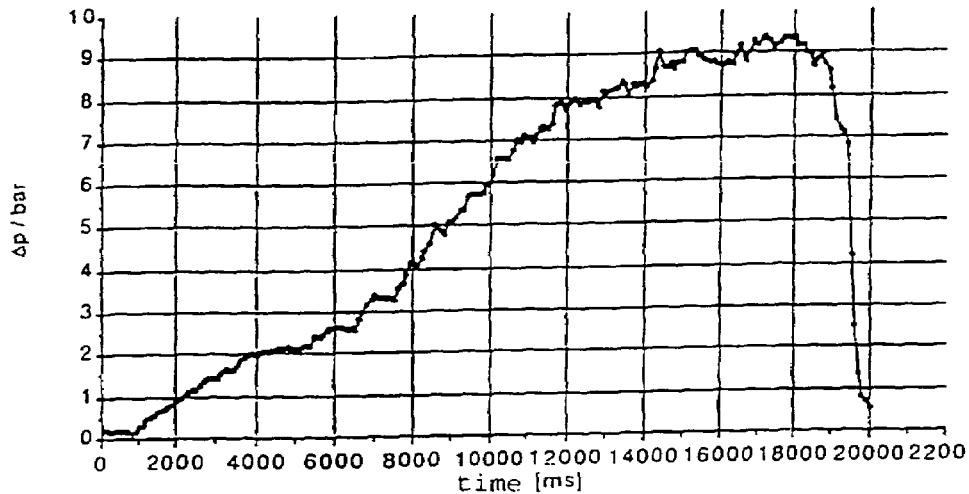
Figure 3C:
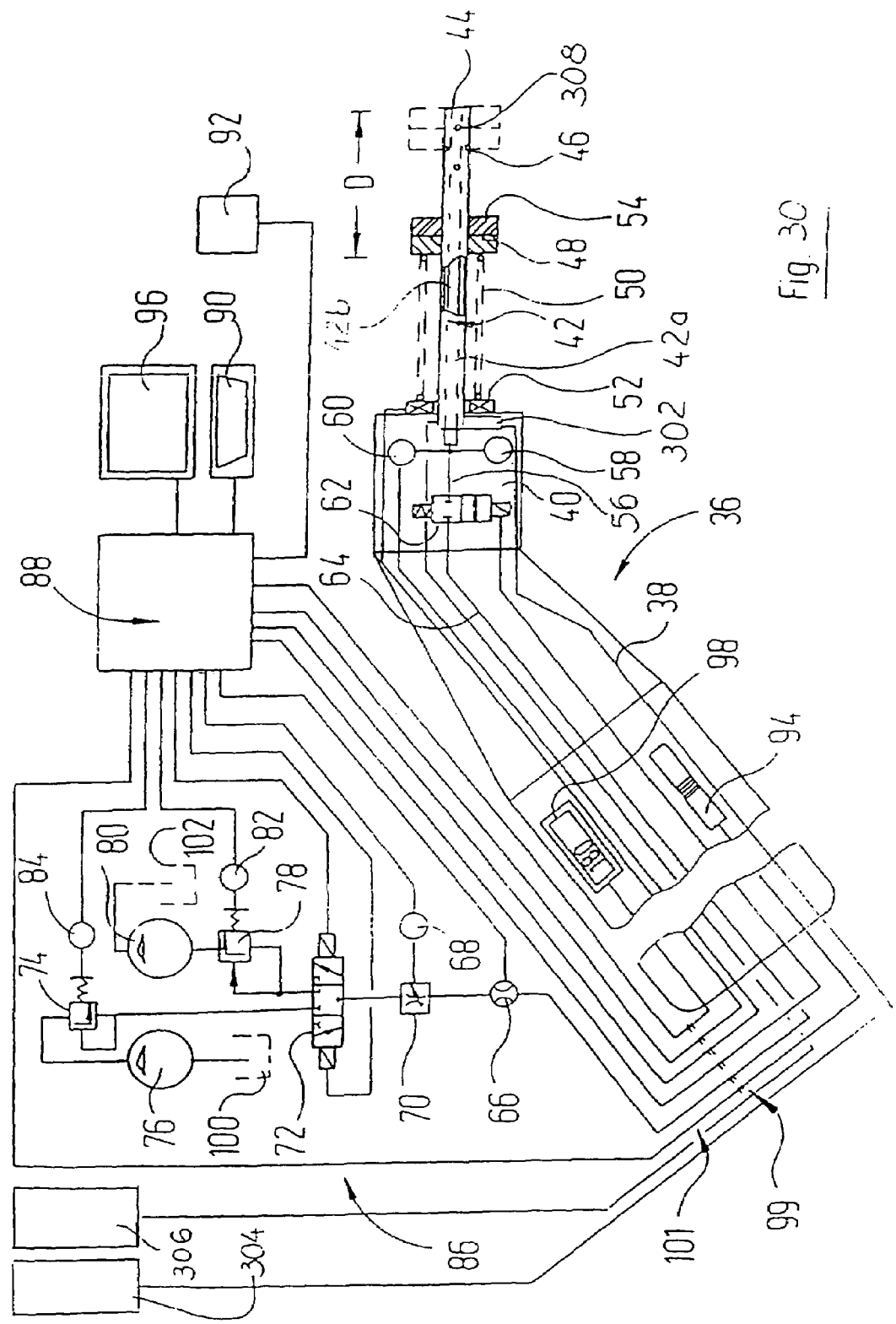

FIGS. 7–10: similar views as in FIG. 6, in which modified diagnostic apparatuses are shown;

FIG. 11: a diagrammatic representation of an optical diagnostic apparatus which has been modified once again and which can be used in conjunction with a working channel passing through the tooth and cutting the diseased tissue region;

FIG. 12: a representation similar to FIG. 4 but in which a clean treatment apparatus is depicted;

FIG. 13: a diagrammatic representation of a treatment apparatus with a particularly simple mechanical design;

FIG. 14: a diagrammatic representation of an aspiration device for excess diagnostic or treatment medium;

FIG. 15: a diagrammatic representation of a treatment apparatus for diseased tissue regions located on the tooth surface;

FIG. 16: a perspective representation of a drilling apparatus with which a working channel leading from the tooth surface to an interior diseased tissue region can be produced;

FIG. 17: a lateral view with a partial axial section of a filling article which can be inserted into a working channel produced in a tooth and which contains a treatment medium for long-term delivery;

FIG. 18: a longitudinal section through a treatment article which is able to keep a working channel produced in a tooth open for a lengthy period, and adjacent tissue regions, it also being possible for the treatment article subsequently to form part of a definitive closure or of a definitive filling of the working channel after either remineralization has succeeded or after reinfiltration;

FIG. 19: a lateral view of the working end of an excavation tool for radial widening of a working channel produced by a drill;

FIG. 20: a lateral view of the working end of a modified excavation tool;

FIG. 21: a lateral view of the working end of an excavation tool modified once again;

FIG. 22: a lateral view in partial section of a modified sealing point between a working section of a diagnostic or treatment apparatus and a working channel produced in a tooth;

FIG. 23: a diagrammatic lateral view of an ultrasonic drilling apparatus for producing a working channel in a tooth;

FIG. 24: an axial partial section through an excavation tool modified once again;

FIG. 25: a frontal view of the excavation tool shown in FIG. 24;

FIGS. 26–29: diagrams which illustrate how the pressure in working channels leading to tooth regions differing in the severity of damage changes as a function of time on use of a diagnostic apparatus as shown in FIG. 4;

FIG. 30: a representation similar to FIG. 4 of a combined drilling, diagnostic and treatment apparatus; and FIG. 31: a representation comparable to a flow diagram of the procedure for treating approximal caries with use of a diagnostic apparatus and, where appropriate, treatment apparatus, and of diagnostic and treatment media as disclosed herein.

In FIG. 1, a molar tooth is designated overall by 10. This has a grinding surface 12 (occlusal surface) at the top, a malar, outer or buccal contour surface 14, an inner or oral contour surface 16, an anterior or approximal-mesial contour surface 18 pointing towards the front end of the jaw, and a posterior or approximal-distal contour surface 20.

An adjacent molar tooth is shown at 22.

The molar tooth 10 has a diseased tissue region (lesion) 24 in the region adjacent to the molar tooth 22. For the purposes of the description and for the sake of simplicity it is assumed that the lesion has essentially the shape of an ellipsoid of rotation, it being self-evident that in practice lesions on the one hand are usually nonsymmetric structures and, in addition, do not have distinct contour surfaces, the boundary between diseased and healthy tissue being fluid. In may further be assumed that the lesion 24 not only affects the tooth enamel cap designated by 28 in FIG. 1 but also extends into the dentine volume 26 of the molar tooth 10. The outer surface of the tooth enamel cap 28 as yet shows negligible structural incursions, however.

The location and dimensions of the lesion 24 depicted in FIG. 1 is [sic] derived roughly from a radiograph made of the molar tooth 10. It is not possible to decide on the basis of the X-ray image whether the lesion 24 comprises a tissue region with such severe damage that structural incursions, porosities or even a cavity is present, requiring reinfiltration or even conventional management with a filling after removal of the caries. The lesion 24 might also be only an incipiently damaged tissue region which can be returned to the healthy state by remineralization.

In order to obtain information about the pathological state of the tissue region 24, a hollow core borer 30 (compare FIG. 2) is used to drill a working channel 32 from the buccal contour surface 14 through the tooth enamel cap 28 and the dentine volume 26 until the end of the channel is, according to the crude information derived from the X-ray images, located in healthy dentine again, on the other side of the diseased tissue region 24, as depicted in FIG. 2.

The procedure for more accurate resolution of the size and severity of the lesion can be as follows:

Stepwise drilling toward the center of the lesion is performed, and successive measurements are made at several points extending from the healthy to the diseased tissue, preferably by determining leakages from the drilled hole through diseased tissue to the tooth surface ("natural caries access").

The drilled core and analysis thereof provides certainty that the drilling has not completely passed by the relevant lesion. Analysis of the drilled core is an optional and not indispensable step. If it emerges from the leakage measurement that the tissue structure is not yet severely compromised, the lesion can be healed by remineralization.

If the structural damage to the access (natural caries access) is so extensive that remineralization is no longer possible, a leakage will be detectable suddenly in one step of the stepwise drilling of the working channel and the particular subsequent measurement.

The defect which can no longer be healed by remineralization can then be worked to remove severely damaged parts of tissue. This can take place by use of ultrasonic working tools or mechanical tools, where appropriate with assistance by abrasive particles suspended in liquid. Conditioning of the defect can then be followed by reinfiltration of liquid and subsequently setting material.

Withdrawal of the core drill 30 from the molar tooth 10 is accompanied by withdrawal of the drilled core 34 enclosed by the latter. The drilled core 34 can be ejected axially from the hollow core drill 30 by a suitable tool, for example a thin wire, and the diseased tissue regions can be rapidly distinguished from the healthy tissue regions by inspection (where appropriate with staining, for example with fuchsin). It is possible where appropriate for chemical and/or biological analyses additionally to be carried out on the various sections of the drilled core 34.

FIG. 3 shows the working channel 32 which has been produced by the core drill 30 and runs close to the approximal contour surface of the molar tooth 10.

The working channel 32 can initially be used to introduce a diagnostic apparatus into the interior of the tooth, with which it is not only possible for healthy and diseased tissue regions to be distinguished but also possible to recognize whether diseased tissue regions can be healed by remineralization. Diagnostic apparatuses of this type are now firstly described with reference to FIGS. 4–11, with the apparatus shown in FIG. 4 also being a treatment apparatus.

The working channel 32 can also be used for introducing or siting treatment apparatuses like those explained hereinafter with reference to FIGS. 12–15, to which the combined diagnostic and treatment apparatus shown in FIG. 4 also belongs.

Where a treatment apparatus is mentioned in the Claims and the present description, this is intended equally to mean an apparatus which is used for mechanical working, hydrodynamic working, ultrasonic working, laser working or other working of hard tissue, which delivers a treatment medium assisting the remineralization or which delivers a medium serving for reinfiltration.

It is also possible to insert into the working channel 32 treatment articles which bring about long-term delivery of treatment media, as well being explained hereinafter with reference to FIG. 18.

A diagnostic and treatment handpiece for carious dental tissue is designated overall by 36 in FIG. 411.

The handpiece 36 has a grip part 38 which has similar axial and radial dimensions as a drill handpiece. A working head which is designated overall by 40 is attached to the grip part 38. This head has a hollow-cylindrical working section 42. The latter has at its end a stop plate 44 which is connected by three thin spacer bars 46 with an equal radial distribution to the open end of the cylindrical working section 42. This ensures that the working section 42 cannot be introduced so far into the working channel 32 that its open end is closed by the floor of the working channel 32. The stop plate 44 also forms a fluid barrier in the working channel 32 extending as far as its wall surface.

A seating disk 48 which is engaged by one end of a helical spring 50 is displaceably guided on the outer surface of the working section 42. The other end of the spring is supported on the front wall of the working head 40 via a dynamometer 52 which is only indicated diagrammatically.

The seating disk 48 in turn carries a sealing disk 54 made of elastomeric material.

The interior of the working section 42 is connected to a working line 56 of the working head 40, to which line are connected a small pressure reservoir 58 and a pressure gauge 60.

The working line 56 is connected via a 2/2 solenoid valve 62 which is spring-pretensioned in the closed position to a line 64 which is connected via a flow gauge 66 and a flow restrictor 70, which can be adjusted by a motor operator 68, to the outlet of a 3/3 solenoid valve 72. The two inlets thereof are respectively connected via a pressure controller 74 to the outlet of the compressor 76, and via a pressure controller 78 to the inlet of an aspirator 80. The controlled pressures of the pressure controllers 74 and 78 can be adjusted electrically by motor operators 82, 84.

Components 62–84 just described form a supply and disposal unit 86 which, in the exemplary embodiment considered firstly herein, supplies air under controlled pressure or reduced pressure to the handpiece 36.

A control and evaluation unit 88 is connected to the electrical output signals of the dynamometer 52, of the pressure gauge 60 and of the flow gauge 66. Further input signals are received by the control and evaluation unit from a keyboard 60 in order to execute on various diagnostic and testing programs which are filed on a mass memory 92 which can be, for example, a hard disk.

A slider control 94 is provided on the handpiece 36 to control the intensity of the fluid supply thereto, and is connected to another inlet of the control and evaluation unit 88.

Interfaces on the output side of the control and evaluation unit 88 are connected to the solenoid valves 62 and 72 and to the motor operators 68, 82 and 84.

The control and evaluation unit 88 is connected to a display screen 96 for displaying the current working conditions and results of measurements. Output of the working parameter which is currently of most interest to the treating clinician is additionally possible on a small LCD display 98 which is carried by the grip part 38. This will usually be the fluid pressure adjusted by the slider control 94, but input of another working parameter on the LCD display 98 is also possible for specific applications, for example the depth of penetration, derived from the output signal of the dynamometer 52, of the working section 42 into the working channel 32. This distance is indicated by D in FIG. 4, where the position taken by seating disk 48 and sealing disk 54 in the unloaded state is represented by broken lines as reference position. This reference position can be preset by the stopping action working section 42.

The handpiece 36 is connected by a rotary coupling, which is designated overall by 99 and is indicated only diagrammatically, to a supply cable 101 which contains the various tubes and lines leading to the supply and disposal unit 86 and to the control and evaluation unit 101.

The handpiece 36 described above is able to investigate, together with its supply and disposal unit 86 and with the control and evaluation unit 88, the tissue surrounding the working channel 32 for disease and remineralization ability. It is employed for this in the following way:

A "porosity positive pressure measurement" measuring program is loaded from the mass memory 92 into the control and evaluation unit 88 via the keyboard 90. This program adjusts the pressure of the compressed air supplied to an inlet of the solenoid valve 72 to a standard value suitable for tissue porosity measurements. This can be, typically, between 1.2 and 1.5 bar and, if required, can be altered by actuating the slider control 94 to larger (up to 8 bar) or smaller values by the dentist.

The dentist then places the handpiece 36 on the side of the molar tooth 10 to be investigated and pushes the hollow-cylindrical working section 42 progressively into the working channel 32. During this, the seating disk 48 and the sealing disk 54 remains [sic] behind, and the latter is widened somewhat by pressure, resulting in a sealing point between the outer surface of the working section 42 and the buccal contour surface 14 of the molar tooth 10. It is then possible to start with a measurement procedure, and this is detected by the control and evaluation unit 88 by an appropriate output signal from the dynamometer 52. It then switches the solenoid valve 72 into the position in which the output of the pressure controller 74 is connected to the outlet side working opening of the solenoid valve 72. This means that compressed air under the required pressure is available at the inlet of the solenoid valve 62.

The control and evaluation unit 88 then opens the solenoid valve 62 at regular intervals so that the interior of the working section 42, the working channel 32 and the tissue surrounding it, and the pressure reservoir 58 are filled with compressed air. The open state of the solenoid valve 62 is maintained for a period sufficient for complete filling of the pressure reservoir 58, of the working section 42 and of the working channel 32 section communicating with the latter. It is possible for this purpose either to choose a period which experience has shown to be sufficient, or for the control and evaluation unit 88 to establish when the output signal of the pressure gauge 62 remains constant. The solenoid valve 62 is then closed, and the control and evaluation unit 88 records the fall in the output signal from the pressure gauge 60. When there is a good seal between the outer end of the working channel 32 and of the working section 42, the pressure drop detected by the pressure gauge 60 is attributable to air leakages which take place through the diseased tissue region 24 to the surrounding atmosphere. A more advanced destruction of this tissue region results in a faster decline in pressure.

Previous measurements and calibration measurements reveal the limiting decrease in pressure after which the diseased tissue is no longer capable of remineralization. If no pressure drop can be detected or the pressure drop is low, remineralization treatment can be carried out with good prospects of success.

The measurement outlined above can equally be carried out with the working line 56 exposed to a negative pressure in analogy to the description above for exposure to positive pressure. In this case, the control and evaluation unit 88, in a "porosity negative pressure measurement" program input from the mass memory 92, simply places the solenoid valve 72 in the other working position in which the pressure controller 78 is connected to the outlet of the solenoid valve 72. The control and evaluation unit 88 then records the pressure rise occurring on the pressure gauge 66 after closure of the solenoid valve 62. Negative pressures (pressure reductions from normal pressure) of between 100 and 500 mbar have proved suitable for standard investigations. It is self-evident that these pressures can be further increased or reduced in the individual case to be most favorable in relation to the porosity of the diseased tissue region and in relation to the accuracy of measurement in the individual case.

In a modification of the exemplary embodiment described above, instead of air being used as gas for measuring the porosity of the diseased tissue region 24, it is also possible to use an inert gas or another gas which simultaneously has a therapeutic effect, for example chlorine-containing air.

In a further modification of the exemplary embodiment described with reference to FIG. 4, it is also possible to use, instead of a gas for measuring the porosity of the diseased tissue region 24, a liquid, for example water or a physiological sodium chloride solution, or a solution with therapeutic activity.

In this case, the component 76 is then a liquid delivery pump and component 80 is a liquid suction pump. The delivery pump 76 aspirates the diagnostic liquid out of a storage container 100 which is indicated in FIG. 4 by dotted lines. The control and evaluation unit 88 then determines the porosity of the diseased tissue region 24 starting from the output signal of the flow gauge 66. The output signal of the pressure gauge 60 can be used in addition to indicate when residual air in the handpiece and in the tissue is displaced. In a simplified version of a handpiece working only with diagnostic liquid the pressure reservoir 58 and the pressure gauge 60 can also be omitted. The handpiece shown in FIG. 4 is, however, equally suitable for measuring tissue porosity using gaseous and liquid fluids.

If operation of the control and evaluation unit 88 depends on the output signal of the flow gauge 66, the liquid flow which is measured in the stationary state by the flow gauge 66 and emerges continuously through the diseased tissue region 24 into the tooth surroundings is a measure of the severity of the disorder or the degree of demineralization or of the porosities or cavities present.

In a combined diagnostic operation mode, it is also possible to examine the [sic] time behavior of the liquid flow measured by the flow gauge 66, in which case the larger flows obtained until the liquid flow is stationary corresponds [sic] to an initial displacement of air from the working channel sealed by the diagnostic apparatus. This displacement likewise takes place through the diseased tissue region and into the latter.

It is possible by using liquids of differing viscosity to displace the measurement range of the diagnostic apparatus shown in FIG. 4: low-viscosity liquids such as water are very suitable for measuring less porous diseased tissue regions, whereas diagnostic liquids with a higher viscosity can be used for more porous tissue regions.

It is possible additionally to add to the diagnostic liquids marker substances which are absorbed differently by healthy and diseased tissue and facilitate visual and/or analytical differentiation of diseased and healthy tissue. These include, for example, dyes such as fuchsin, it being possible to use the latter, for example, as a 0.5% strength basic solution in propylene glycol.

Other suitable marker substances are electrolytes, X-ray contrast agents, radionucleides [sic] etc.

If a hollow drill is used to produce the working channel (conventional drilling appliance with rotating hollow diamond drills such as oscillating preparation appliances), the hollow drills can simultaneously serve as probe sections supplying or removing fluid when a connection is made between the interior of the hollow drilling tool and a fluid source or a fluid sink by a suitable design of the drilling tool holder. It is then possible in this case for the drilling appliance also to represent a diagnostic apparatus and/or treatment apparatus as has been described above with reference to FIG. 4.

It is possible in this way particularly conveniently to advance the working channel by advancing the drilling tool stepwise in the direction of the suspected lesion and, at the same time, without changing the apparatus, carrying out the fluid-dynamic diagnostic determination of the health of the tissue after each increment in the advance. This greatly facilitates the work overall.

The apparatus shown in FIG. 4 can also be employed as treatment apparatus in order to carry out a liquid exchange in porous diseased tissue, in particular to force fluoride-containing liquids into these tissue regions. It is also possible in addition for other treatment liquids, which prepare the diseased tissue for fluoridization to be forced into the diseased tissue using the handpiece shown in FIG. 4 and, after a preset treatment time, to be aspirated out of this tissue or forced through the tissue. It is simple to use for this purpose storage containers 100 which contain a treatment liquid in place of a diagnostic liquid.

Possible examples of such treatment liquids are:

a) Irrigation liquids: these remove tissue fragments resulting on production of the working channel or on the basis of the disorder, and bacteria from the diseased tissue region. If the irrigation liquids are supplied with oscillation, it is possible in this way also to destroy the cell walls of bacteria in the diseased tissue region or to damage the surfaces of the bacteria so that they are no longer able to carry out any destructive metabolic activities. It is possible with a rapid change in pressure to obtain hard substance-ablating cavitation effects.

b) Disinfecting solutions such as, for example, chlorhexidine solutions: these chemically destroy bacteria found in the diseased tissue region.

c) Adhesives: (for example solutions containing carboxyl groups, modified polyacrylic acid solutions, solution mixtures containing acrylate mono- or polymers or solvent- (for example acetone-) containing monomer or polymer solutions etc.)

d) solutions which dissolve organic tissue residues, for example sodium hypochloride [sic] solutions in concentrations below 6% by weight, preferably below 3% by weight, once again preferably around 1% by weight and N-monochloro-DL-2-aminobutyrate-containing solutions.

e) Etching solutions: these include aqueous calcium chelating agents, for example EDTA solutions below 50% by weight, preferably around 20% by weight. These solutions make chemical ablation of very substantially demineralized tissue possible, and inorganic and organic acids.

f) Liquids containing inert particles: these introduce small inert particles into the porous structure of the diseased tissue, resulting in sealing of the latter. Particles of this type can also be wedged into the boundary layers and can also be incorporated into the reinfiltration volume in order in this way to form the basis for additional adhesion effects of the reinfiltrated material on the surface of the particles wedged in the hard tissue. Particles of this type may also be useful for cleaning, accelerated ablation, preparation or conditioning of the diseased tissue region if they are moved towards the diseased tissue by exposure to changes in pressure or by exposure to ultrasound.

Suitable inert particles are glass particles, calcium phosphate particles, hydroxyapatite or fluorapatite particles, calcium fluoride particles, salt particles, carbonate particles, fluorspar particles, ceramic particles, plastic particles or composite particles. Preferred particle diameters in this connection are between 0.5 and 2 $\mu$m or else up to about 5 $\mu$m in order to fulfill the sealing and bridging function mentioned above, while particles with a larger average particle size are suitable for more severely damaged diseased tissue regions and for mechanical working of tissue (5–10 $\mu$m up to 20, 50 or 100 $\mu$m).

The particle sizes are chosen in accordance with the application:

If the abrasive properties of the particles are of interest, particles with average or larger diameters from the scale indicated above are chosen. If, on the other hand, it is wished to block open dentinal tubules in order to produce an internal diffusion barrier (whether the defect surfaces are on the outside of sensitive necks of teeth or facing inwards on the pulp), the particle sizes used correspond to the smaller size ranges mentioned above.

In both cases, inert particles of this type can form adhesive substrates.

It is also possible where appropriate to use mixtures of different particles which have different average particle diameters, these different average particle diameters being chosen for optimal functioning for various tasks among those mentioned above.

f) Solutions acting on the pulp: these solutions contain active substances which are able to assist healing processes in the pulp and are used when the diseased tissue region to be remineralized is adjacent to the pulp. Examples of such active substances are BMP (bone morphogenetic proteins) and calcium hydroxide ($Ca(OH)_2$) for stimulating hard tissue formation and K and Sr compounds for desensitizing the pulp.

g) Remineralization-promoting liquids: these liquids contain active substances which assist remineralization. Thus, for example, fluorides shift the de/remineralization equilibrium in favor of remineralization, even in an acidic environment (down to pH 4.5). Specific bacteriostatic or bacteriocidal effects like those provided, for example, by chlorhexidine also assist remineralization (elimination of acid-producing bacteria). The remineralization itself is preferably effected by minerals which are dissolved in the saliva and reach the lesion via the "natural caries access".

h) Liquids, gels or paste used for the reinfiltration: after setting in the porous structures and/or cavitations of the lesion and/or in the cavities produced by preparation and/or in adjacent tissue structures, these form a hard tissue substitute material.

The abovementioned treatment liquids can in each case be aspirated into a storage container 100 successively in the desired sequence from the delivery pump 76 and be forced into the working channel 32 and thus into the diseased tissue region 24.

When a diseased tissue region is in flow connection with the outer surface of the tooth, it is sufficient to keep the treatment liquid under pressure continuously; the treatment liquid then flows through the diseased tissue region to the outer surface of the tooth.

When there is no such flow connection, because the diseased tissue region is surrounded by healthy tissue, the liquid exchange between the diseased tissue and the working section 42 of the handpiece 36 is assisted by selecting a "treatment pressure and suction" working program of the control and evaluation unit 88, with which the solenoid valve 72 is switched intermittently between its two working positions, by which means treatment liquid is intermittently forced into the diseased tissue and sucked out of the latter again. Amounts of liquid which have been sucked back are delivered by the suction pump 80 to a collecting container 102.

The various liquids mentioned above are thus used for the following purposes:

Diagnosis: if a test of whether a lesion is permeable to the surface of the tooth ("natural caries access") is affirmative, it is tested whether the permeability is so large that remineralization is no longer possible.

Treatment to assist remineralization: remineralizable tissue surrounding a measurement point forms a good diffusion barrier. Introduction of a treatment liquid under continuous pressure results in diffusion of the active substances present in the treatment liquid over a prolonged period into the surrounding tissue, which prepares the latter for better remineralization. The exchange between tissue liquid and treatment liquid can be assisted by a pumping action wherein the treatment liquid is alternately placed under positive pressure and negative pressure or is applied with exposure to sound or ultrasound.

Treatment to prepare for reinfiltration: irreversibly damaged tissues contained within the lesion volume are removed by exposure to rapid changes in pressure or "water jet action", or by exposure to ultrasound (where appropriate assisted by abrasive particles). The treatment medium serves in this case as coupling and transport medium. Where the treatment medium additionally contains active substances, the active substances are also introduced into the remaining tissue structure, where they are then able to display their chemical or biological effect.

Irrigation action: if the permeability of the diffusion barrier is large, the treatment media can also be forced continuously through the lesion (pure irrigation or removal or drying action).

Reinfiltration: a settable liquid material is introduced, and this displaces where appropriate any residues still remaining of other treatment media and forms, after setting, a tooth substitute material.

To simplify a multistage treatment process, it is also possible for a plurality of the treatment liquids to be mixed in a storage container 100 and supplied together to the diseased tissue region.

It is self-evident that a storage container 100 for treatment medium is in practice not an open vessel but, on the contrary, a sterile bag which is connected to the intake line, which is designed as needle, of the delivery pump 76.

It is evident from the above description in connection with FIG. 4 that the apparatus shown therein is a combined diagnostic and treatment apparatus which is suitable for diagnosis optionally with gaseous and liquid diagnostic media and for treatment optionally with gaseous and liquid (or at least briefly made free-flowing) treatment media.

Conversion of the electrical output signals assigned to rises in pressure, falls in pressure or liquid flows and changes thereof into an [sic] electrical signals corresponding to the severity of the disorder in the diseased tissue region 24, which are displayed on the display screen 96, is effected by the control and evaluation unit 88. In this case, the control and evaluation unit can, on the one hand, operate in accordance with algorithms derived from the laws of fluid motion; however, the control and evaluation unit can instead or in addition also operate in accordance with cross-reference tables obtained on the basis of earlier investigations or measurements on test materials. It is moreover possible to use different cross-reference tables which take account of different types of teeth (molar teeth, incisor teeth), the patient's sex and the patient's age. These tables are filed in the mass memory 92, and the one required in each case for a specific measurement is loaded by the control and evaluation unit 88.

The mass memory 92 also contains various measurement programs (for example for gaseous diagnostic media and liquid diagnostic media varying in viscosity). Finally, the treatment programs which specify the control of the solenoid valves 62, 72 and the control of the working pressures via the motor operators 82, 84, and a flow limitation through the flow restrictor 70 by the motor operator 68 for the various treatment media are also filed on the mass memory 92.

FIG. 5 shows a handpiece (and assigned supply and evaluation units) which is used only for diagnosis. Apparatus components which have already been explained above with reference to FIG. 4 are again provided with the same reference numbers and are not described again in detail.

The diagnostic apparatus shown in FIG. 5 operates in a tactile manner and has a measuring point 104 which can be moved in the radial direction through a lateral window 106 which is provided in the peripheral wall of the cylindrical working section 42.

The measuring point 104 is carried by a short lever 108 which is pivotably mounted at the end of the working section 42. An actuation bar 112 acts on the lever 108 via an intermediate rod 110 and is connected to a small working cylinder 114. The latter is pretensioned by a spring in an retracted position and can be connected via the solenoid valves 62, 72 to the outlet of the compressor 76.

A position indicator 116 is assigned to the working cylinder 114. The output signal therefrom is thus a criterion for the radial position of the measuring point 104.

The working section 42 is rotatably mounted in the working head 40 and carries a toothed wheel 118 which engages with a pinion 120 which is rotated by a motor operator 122. It is possible in this way to rotate the angular position of the window 106 and thus the measuring site of the measuring point 104 around the axis of the working channel 32. The axial position of the measuring site can be preset by more or less strong compression of the helical spring 50. This means that the diagnostic apparatus can measure the hardness of the tissue overall with resolution in the axial direction and in the radial direction. The angular position of the window 106 can in this case be derived by the control and evaluation unit 88 from the preceding excitation of the motor operator 122, for example in the case of a stepping motor from the number of control pulses previously fed to the latter and acting in the forward and backward directions.

The diagnostic apparatus shown in FIG. 5 can be operated in two different modes of operation:

In the first mode of operation, the control and evaluation unit 88 gives a fixed pressure to the compressed air supplied to the working cylinder 114, and the depth of penetration of the measuring point 104 into the tissue at the various measurement sites is measured via the output signal from the position indicator 116.

In the second mode of operation, the control and evaluation unit 88 successively increases the pressure preset by the pressure controller 74 via the motor operator 84 until the position indicator 116 provides a preset output signal. The pressure at which the appropriate preset depth of penetration of the measuring point 104 is obtained is then a measure of the hardness of the tissue.

The control and evaluation unit 88 can show the various measurements in the axial and radial direction graphically on the display screen, for example in the form of an image of the working channel 32 on whose wall surface the various hardnesses are represented by different colors. In this way, the dentist obtains clear information about the spatial dimensions of the diseased tissue region and the extent of tissue damage.

In the exemplary embodiment shown in FIG. 5, the supply and disposal unit 86 has been represented in exactly the same way as in FIG. 4, although some of its functions are unnecessary for the handpiece shown in FIG. 5, which is a pure diagnostic handpiece. This is intended on the one hand to express the fact that the diagnostic handpiece shown in FIG. 5 can be connected to the same supply and disposal unit 86 and the same control and evaluation unit 88 in place of a diagnostic handpiece shown in FIG. 4. On the other hand, parts of the supply and disposal unit 86 can also be used with handpieces which result from modification of the handpiece shown in FIG. 5. It is then possible, when a driving liquid is supplied to the working cylinder 114, for the flow gauge 66 also to be used to measure the position of the working cylinder, which then makes it possible to dispense with the separate position indicator 116.

The hydraulic cylinder 114 can also be designed so that it is pretensioned in the extended position under a preset spring force. It is then retracted by the aspirator or the suction pump 80 when the working section 42 in the working channel 32 is axially displaced or rotated. The position indicator 116 measures, after venting of the hydraulic cylinder 114, how far the measuring point 114 penetrates into the tissue under the preset spring force.

FIG. 6 shows the point of a modified working section 42. The measuring point 104 is the sharpened end of a piece of wire 124 which moves in a curved drilled guide 126 in the solid end section 128 of the working section 42. The left-hand end of the piece of wire 124 is firmly connected to the actuation rod 112.

Thus, in the exemplary embodiment shown in FIG. 6, the movement is diverted into a direction with a radial component by the drilled guide 126 in conjunction with the flexibility of the piece of wire 124; otherwise, the measuring point 104 operates in a similar manner to the description for the exemplary embodiment shown in FIG. 5.

Figure 7:
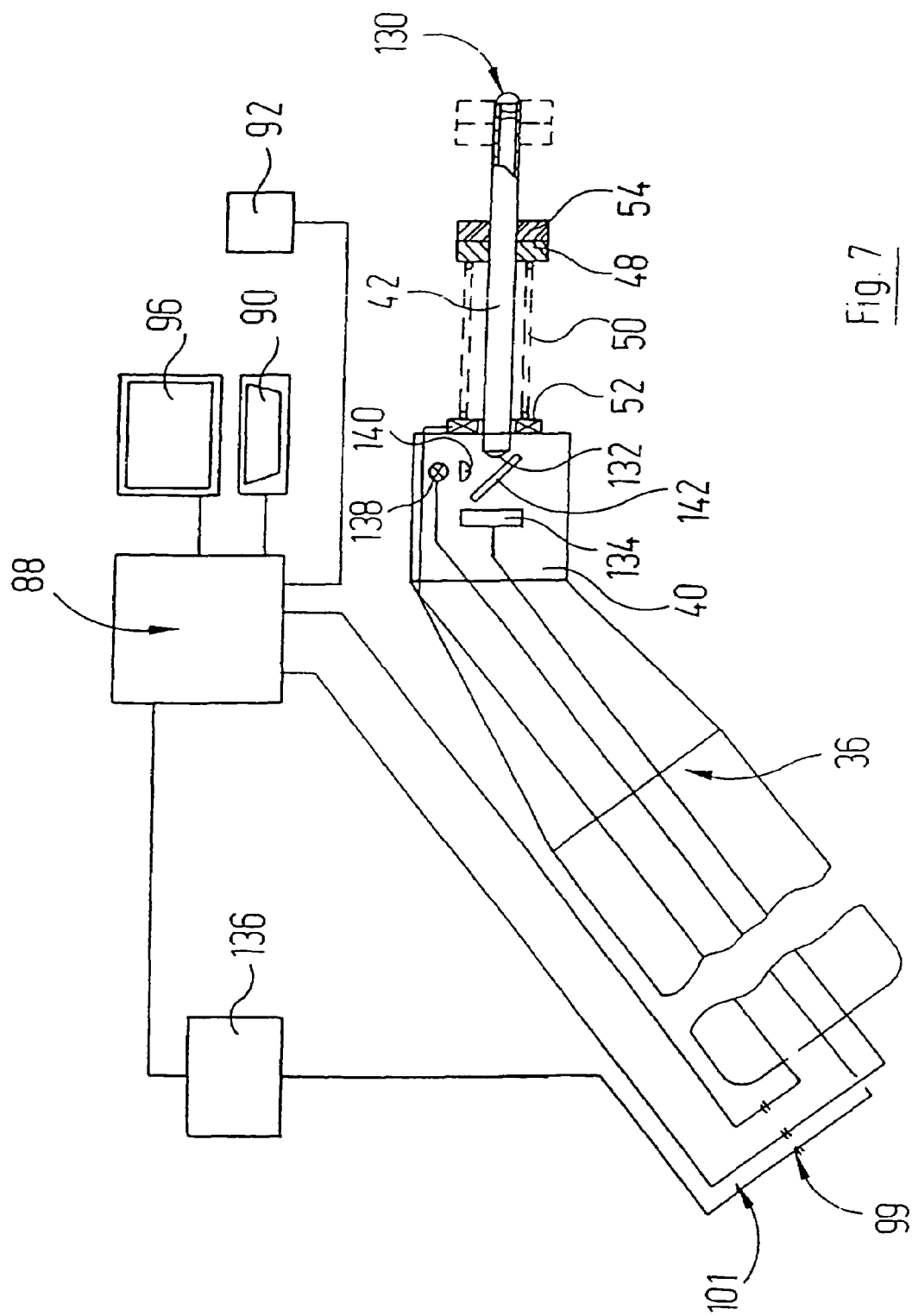

In the exemplary embodiment shown in FIG. 7, the working section 42 has at the front end a lens arrangement 130 consisting of a convergent lens and a divergent lens. The light held at the rear end of the working section 42 is projected by a further lens 132 onto an image converter 134. The latter is connected to a video interface of the control and evaluation unit 88.

The control and evaluation unit 88 supplies via a controlled voltage source 136 a small halogen lamp 138 which directs light through a convergent lens 140 and a semitransparent mirror 142 onto the axis of the working section 42.

In a practical exemplary embodiment it is possible, in a modification, to use a coaxial light guide arrangement which is wholly or partly flexible. A central light guide returns the image of the lesion, produced by the optical system, to an image converter; an outer, hollow light guide supplies illuminating light which is produced by a halogen lamp or a high pressure xenon lamp.

The control and evaluation unit 88 compares the images which are provided by the image converter 134 and which correspond to the direct vicinity of the end of the working section 42 with reference images filed on the mass memory 92 with regard to size of the pores and coloration. In addition, the image produced by the image converter 134 can be inspected by the clinician on the display screen 96. It is possible to determine by this direct inspection and from comparison with reference images the extent of the damage to the tissue located in front of the lens arrangement 130.

Instead of in reflection, measurement is also possible in transmission, that is to say transdentally, in which case the light is supplied through the working channel 32 to the lesion, and the defect is observed from the outside of the tooth using a video camera.

In a modification of the exemplary embodiment shown in FIG. 7, it is also possible to use only the tissue color as differentiating criterion and then to replace the image converter 134 by a light detector and an optical filter arranged in front of the latter (as will be explained similarly with reference to FIG. 11), in which case the working head 43 preferably has a guide in order to be able to put different optical filters in front of the light detector.

Figure 8:
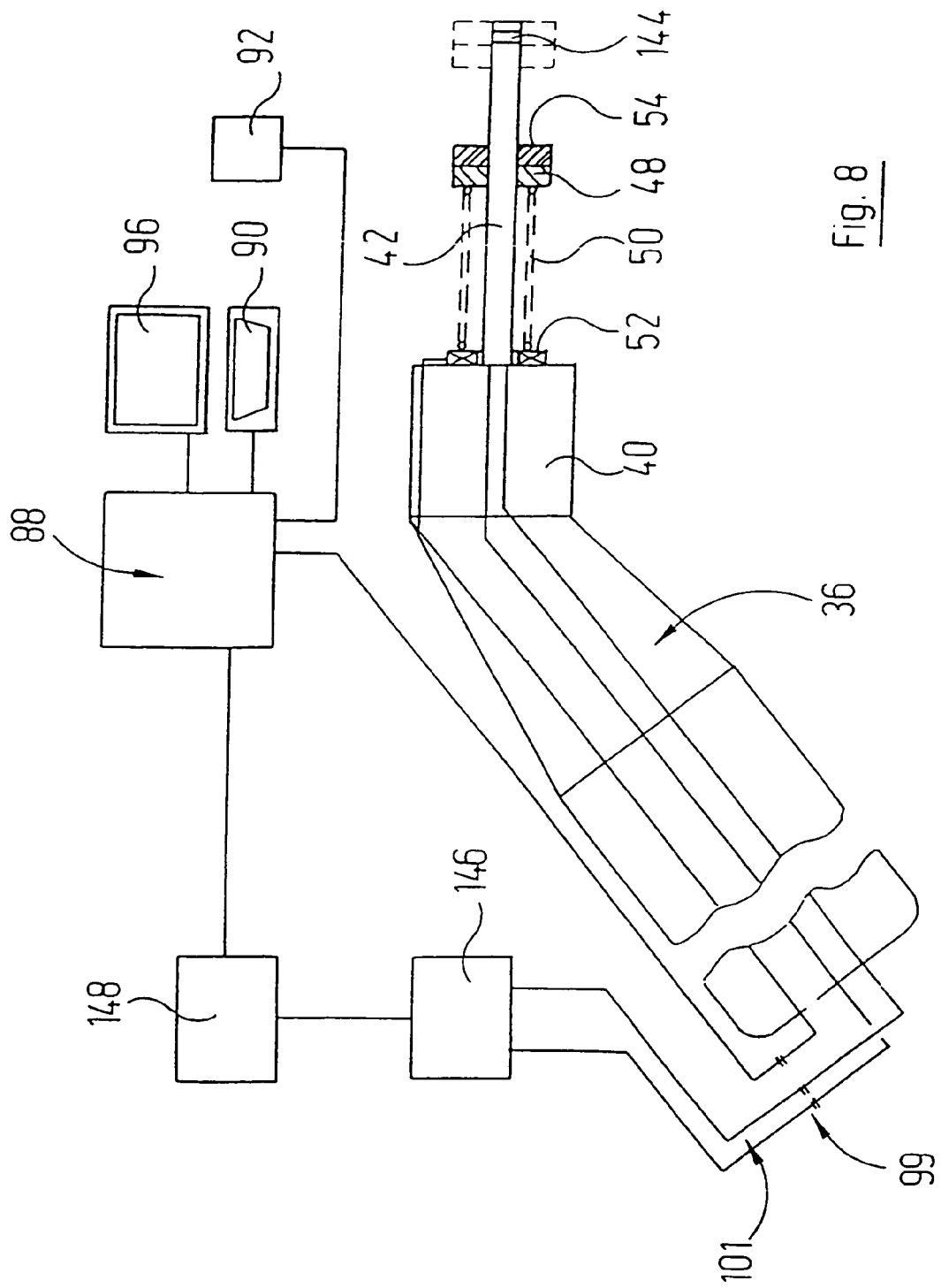

In the diagnostic apparatus shown in FIG. 8, an electroacoustic transducer 144, preferably an ultrasound-delivery piezoelectric transducer, is provided at the end of the working section 42. The transducer 144 is supplied by an operating circuit 146 with appropriately high frequency voltage, and a load sensing circuit 148 is assigned to the operating circuit 146 and provides an output signal which is assigned to the energy supplied to the transducer 144. This energy is larger when the tissue surrounding the transducer 144 absorbs more sound energy. This is precisely the case when the transducer 144 is opposite to diseased tissue which has larger pores and whose material has less elasticity. It is possible in this way, again with axial resolution (dynamometer 52 in conjunction with the helical spring 50), to distinguish healthy and diseased tissue in the lengthwise direction of the working channel 32.

The ultrasonic transducer has been depicted in FIG. 8 as being located at the end of the working section 42. It is self-evident that the ultrasonic transducer can also be provided in the interior of the handpiece 36 and can guide the ultrasound through the working section 42 to the lesion. In this case, the working tip is designed as vibrating sonotrode.

Water is preferably used to produce contact between the ultrasound and the tissue to be diagnosed. This water may already be present in any pores or cavities present in the tissue. It is also possible to put water used for the contact additionally into the working channel. Other media, for example gels, can also be used in place of water.

If not only axial but also lateral resolution of the lesion is required, the ultrasonic transducer can also be attached to the working tip 42 in such a way that it emits in the radial direction. Alternatively, the working tip 42 can be designed as sonotrode deflecting the sound in the radial direction. The spatial resolution of the lesion in the radial direction can also be determined by rotating such ultrasonic measuring points which also (or exclusively) measure in the radial direction.

It has been considered above that diseased and healthy tissue differ in the absorption of ultrasound. This means at the same time that diseased and healthy tissue differ in the reflection of ultrasound. It is thus also possible to determine the severity of local tissue damage by the methods using the time difference between output and reception of an ultrasonic pulse.

As already described above in connection with the mechanical measuring point 104, the spatial dimensions of the lesion can be determined by axial movement and rotation of the measuring point.

A representation of the state of health of the tissue which is easily intelligible for the dentist can be obtained by assigning different colors to tissue regions in different states of health in the representation on the monitor of the image produced by the image converter.

Figure 9:
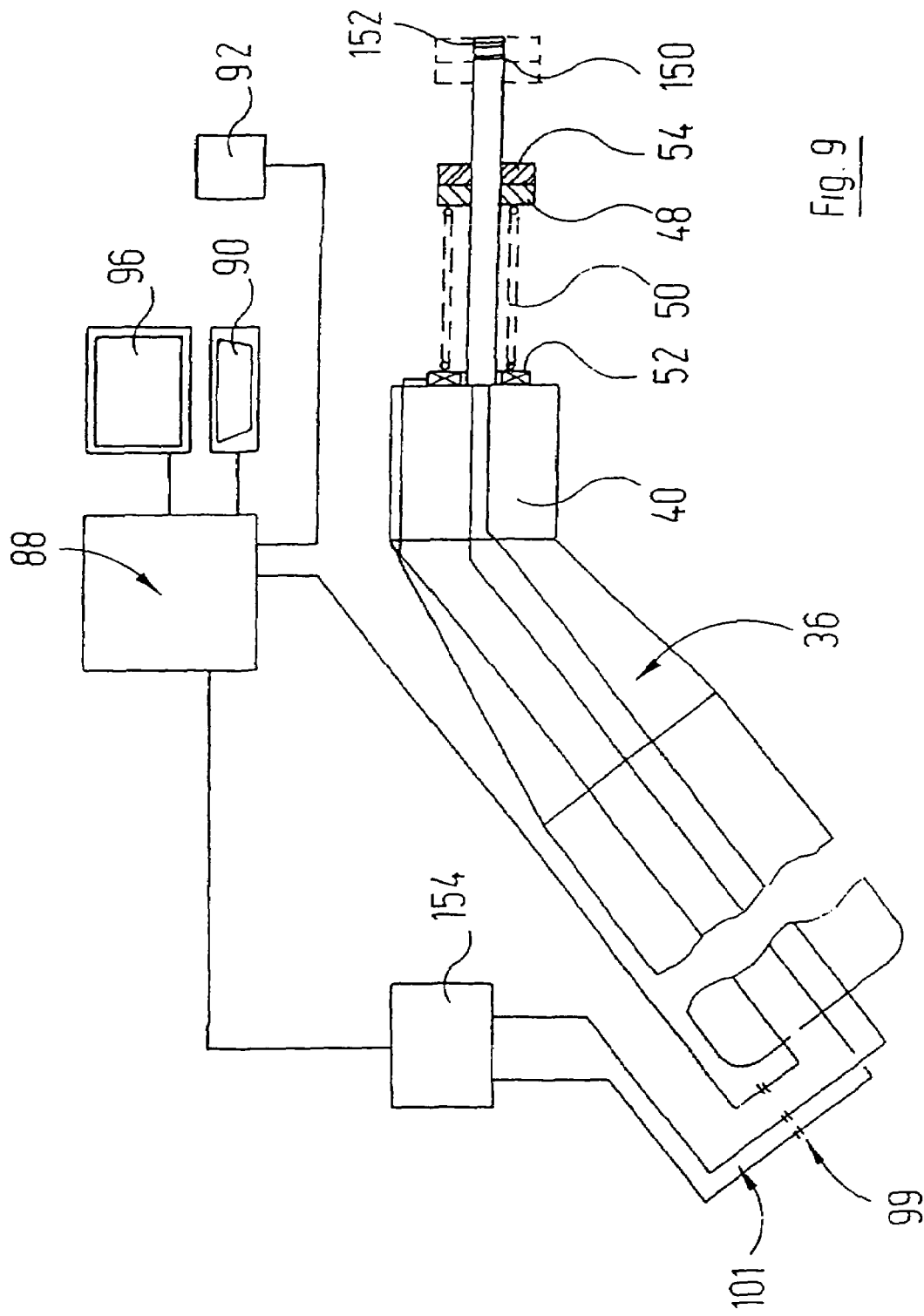

The handpiece 36 shown in FIG. 9 is geometrically very similar to that in FIG. 8 except that the end of the working section 42 carries in place of an electroacoustic transducer two annular, axially-spaced electrodes 150, 152. These are connected to a resistance measurement circuit 154 and/or a frequency analyzer. Under the measurement conditions, the resistance circuit 154 measures, by applying a small voltage to the electrodes 150, 152, the conductivity of those tissue regions which are bridged by the electrodes 150, 152 in the particular position of the working section 42. Since the electrical conductivity of the diseased tissue differs from that of the healthy tissue (because of a difference in pore structure and a difference in filling by liquid), the control and evaluation unit 88, which is supplied with the output signal from the resistance measurement circuit 154, is again able to determine and record the extent of tissue damage in the lengthwise direction of the working channel 42.

A measurement of this type can also be effected transdentally, in which case an electrode is positioned on the outer surfaces of the tooth, for example as thin sheet electrode between the approximal surfaces of the affected tooth and of the adjacent tooth, and is usually clamped there, for example in the region of the "natural caries access" from the approximal direction, and the other electrode is advanced via the working channel into the defect and put into various positions inside the latter. Since healthy enamel is a very good electrical insulator, and the percentage content of water is increased inside enamel with carious lesions, depending on the degree of demineralization, it is possible to draw conclusions about the quality of the hard tissue in this region from the change in electrical resistance and/or the shift in alternating current frequencies.

It is, of course, also possible for this reference electrode to be attached anywhere else on the body or to be held by the patient, for example in the hand.

Figure 10:
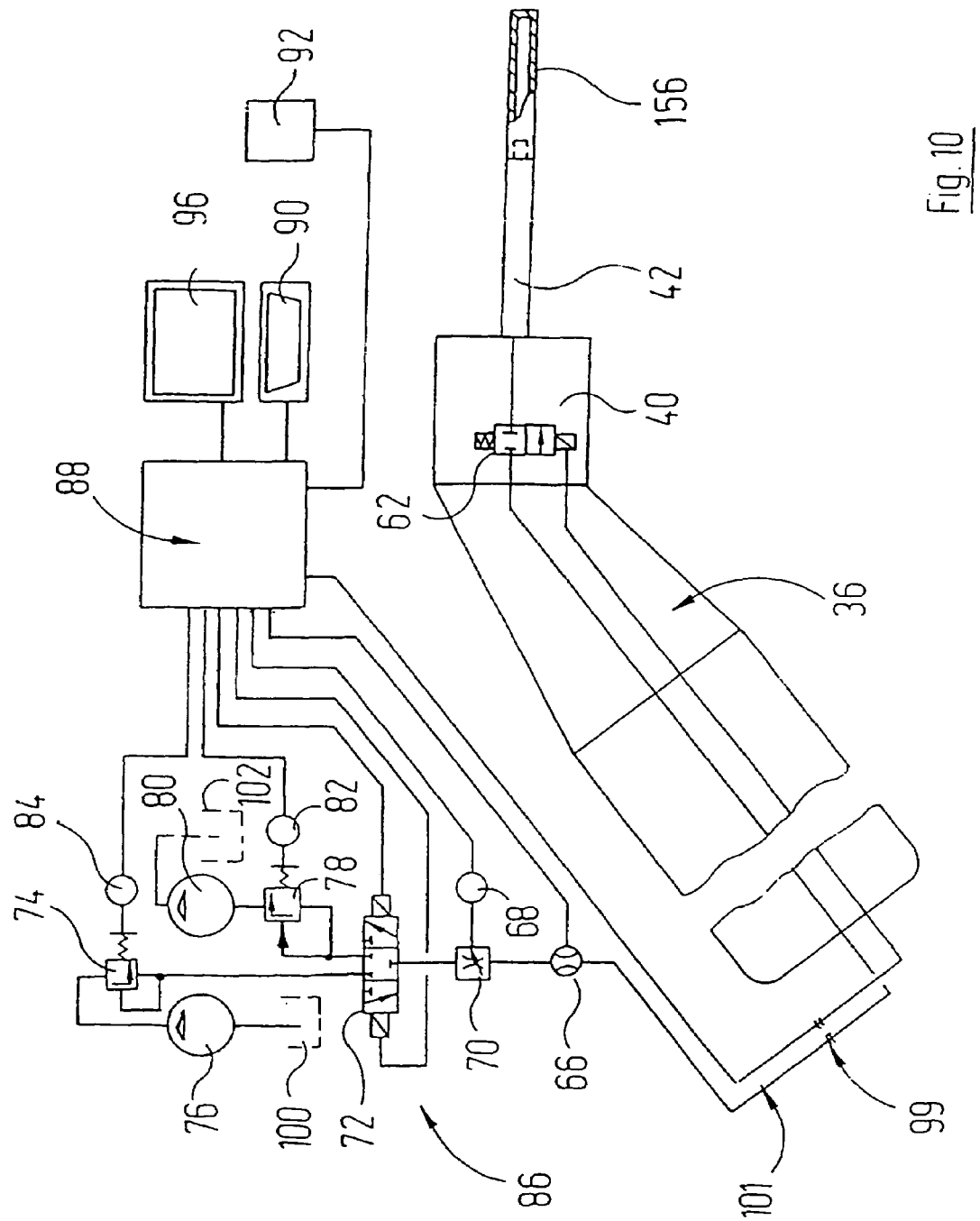

In the exemplary embodiment with a further modification shown in FIG. 10, the working section 42 carries a porous test tube 156 which is produced, for example, from sintered ceramic material. On connection of the interior of the test tube 156 via the solenoid valve 62 and the solenoid valve 72 to the inlet of the aspirator 80, liquid is sucked out of the tissue regions surrounding the test tube. Tissue particles and bacteria present in this liquid are retained in the material of the test tube 156. A residue of aspirated tissue liquid in each case also remains on the wail of the test tube when the aspiration is complete.

Analysis of the materials (tissue liquid, bacteria, tissue fragments) retained in the various sections of the wall of the test tube 156 in turn makes it possible to determine where diseased tissue is present and where healthy tissue is.

A further differentiation of the nature and extent of the tissue disorder can be brought about with the diagnostic apparatus shown in FIG. 10 by initially aspirating liquid from untreated tissue and then, using the possibilities explained above with reference to FIG. 4, successively forcing a diagnostic liquid and/or a treatment liquid (etching liquid, primer liquid) into the tissue, and then again carrying out an aspiration, the latter taking place in each case with new test tubes.

The diagnostic and treatment apparatuses described above have been employed in connection with a working channel 32 which was a drilled pocket, in which case the working channel was more or less open, depending on the extent of the tissue damage, to the surrounding atmosphere through the damaged tissue structure when the tissue was damaged as far as the tooth surface.

It is desirable, especially when the working channel 32 is used only for diagnostic purposes, for the working channel 32 to have only a minimal diameter. It may be advantageous in this case to extend the working channel right through the whole tooth. It is then possible to divide the diagnostic apparatus (and the treatment apparatus) into two parts which are connected to the two ends of such a continuous working channel, as depicted in FIG. 11.

A first monofilament thin light guide 158 with a spherical front surface is inserted into the end which is located on the left in FIG. 11 of the working channel 32 and receives light from a halogen lamp 160 via a convergent lens 162. The light reflected by the tissue surface surrounding the working channel 32 is collected by a light guide 164 with a similar design, and the light delivered by the latter is passed via a lens 166 and an optical filter 168 to a light detector 170. The output signal from the light detector 170 is again taken as a measure of the tissue damage.

The ends of the light guides 158 and 164, and the components cooperating with the latter are accommodated in a housing 172. A thin spacer bar 174 is carried by the end of one of the light guides and holds the ends of the light guides in the working channel 32 at a preset distance.

It is self-evident that it is possible to provide in place of the color filter 168 and the light detector 170 once again an image converter whose output signals is [sic] passed to a unit for image processing and image evaluation.

The transmission principle described in connection with FIG. 11 can also be applied to the treatment: in this case, the light guide 158 corresponds to a thin needle which is connected to a source of treatment fluid, whereas the light guide 164 corresponds to a needle which is connected to an aspiration device.

In another embodiment, which is not shown, of the invention it is possible to apply to one side of the tooth, for a visual check of the tissue, a first handpiece which has an optical system arranged in the working channel, and to provide on the second end of the working channel a handpiece for visually checking the tissue, which has an optical system located outside the working channel. These can be used alternately as light-providing handpiece and light-receiving handpiece and be connected via a change-over switch optionally to the light source or to a light detector or image converter.

FIG. 12 shows a pure treatment apparatus which is used to supply treatment liquid to the diseased tissue region 24 and remove used treatment liquid again from there. The treatment handpiece shown in FIG. 12 essentially corresponds to the combined diagnostic and treatment handpiece shown in FIG. 4 with omission of the handpiece components used for measuring the state of the tissue.

The solenoid valve 62 is now designed as a 3/2 valve, and its second inlet is connected via a releasable plug connection 178 to an injection-molded plastic bellows storage container 176 containing another treatment medium. This treatment medium, which may also have a higher viscosity, is expelled from the storage container 176 by the clinician pressing on the free front surface of the storage container 176. During this, an LED 180, which is controlled by the control and evaluation unit 88, shows him when the solenoid valve 62 is in the position in which the storage container 176 is connected to the interior of the working section 42.

The packaging of the treatment medium in plastic storage containers 176 makes it possible to use a relatively large number of different treatment media in rapid succession. The dead space between storage container 176 and the application site is only small.

The plug connector part 178 is made to be oversized and is initially closed at the end. It is made the length required in each case by cutting off its end section, simultaneously opens the storage container.

In a modification of the exemplary embodiment shown in FIG. 12, the treatment medium can be brought out of the storage container 176 also by a motor controlled by the control and evaluation unit 88, for example a compressed-air or hydraulic motor which can be connected via another solenoid valve to the outlet of the delivery pump 76.

As is evident from FIG. 13, the plug connector part 182, which is present on the storage container 176, of the plug connection 178 can be designed so that it also fits directly into the working channel 32, in which case a conical transitional section 184 of the plug connector part 182 ensures sealing.

In a modification it is possible to use a syringe which is filled with a liquid treatment medium. It is then possible by pushing the plunger of the syringe to feed treatment medium into the working channel 32.

If the diseased tissue region 24 is located very close to the tooth surface, and if the tissue damage is already so severe that a considerable pathway for leakage to the tooth surface is formed, when liquid is supplied to the working channel 32 relatively large amounts of liquid emerge through the diseased tissue to the tooth surface. In order to prevent these amounts of liquid also acting on the adjacent tooth and getting into the patient's mouth, it is possible as shown in FIG. 15 to insert a suction part 200 between the two teeth, in which case the distance between the teeth is temporarily increased where appropriate by a wedge 202. The suction part 200 is a hollow part which is made of rubber or synthetic material and which is connected via a connecting sleeve 204 to a suction line 206. In the main surface located on the left in the drawing, the suction part 200 is provided with a suction orifice 208 which is placed next to the diseased tissue region 24.

A treatment cap 210 (compare FIG. 15) can be provided for treating tissue defects near the surface of a tooth, and this cap has a design similar to a suction cap and a frustoconical boundary wall 212 which, under elastic deformation, represents with its edge a sealing place on the tooth surface. A connecting sleeve 216 is formed on the upper cap wall 214 and can be connected, for example, to the plug connector part 182 of the storage container 176 shown in FIG. 13.

It is possible in this way to treat tissue defects located on the tooth surface with the various treatment liquids mentioned hereinbefore in order for the tissue surface to be prepared for remineralization and to be remineralized or reinfiltrated.

An alternative possibility is to stimulate oscillation in the liquid volume defined by the geometries of the treatment cap, of the connecting sleeve and of the feed lines and contained therein, and to determine the damping of this oscillation by the area of contact with the tooth's hard substance surface in question. If carious tooth hard substance volumes, in particular dentine caries volumes, are connected to the adapted oscillating liquid volume, the result of this is greater damping than with healthy tooth hard tissue, especially an intact tooth enamel covering.

It is also possible with this method to detect quantifiably any hidden caries lesions in the occlusal fissure region. It is also, of course, possible to employ analogously the above-mentioned marker substrates and treatment media in this application.

FIG. 16 shows a drill handpiece 218 into which the core drill 30 shown in FIG. 2 is inserted. The handpiece 218 has a depth stop 220 which is locked in the position set in each case by a fixing screw 222. The depth 220 is set according to the rough position previously determined by X-ray images of the diseased tissue region 24.

The depth stop 220 is adjustably attached by means of a fixing screw 222 to an annular part 224 which is rotatably seated on the tool storage housing 226 of the handpiece 218 and is locked by a fixing screw 228. It is possible in this way to select the orientation of a grip part 230 of the handpiece 218 which is most convenient for the dentist's work, and to select the position of the depth stop 220 which is most favorable in relation to secure support on the tooth to be treated.

The above exemplary embodiments have been explained in connection with gaseous and liquid diagnostic and treatment media.

However, it is also possible to put a solid treatment medium, for example a treatment tube which is shown in FIG. 17 and is designated overall by 232, into a working channel 32 produced as described above. This tube has a hollow-cylindrical main article 234 which may consist, for example, of porous sintered material. A powdered treatment medium 235 (for example a salt or resin-bound active substances) is introduced into the pores of the sintered material and/or into the interior of the main article 234.

The treatment tube 232 also has a head section 236 which is slightly conical and is preferably provided with a countersink 238 in the center.

To use the treatment tube 232 it is pushed into the working channel 32 and forced into the latter so that the head section 236, which is conical on its peripheral surface, produces a sealing place with the edge of the working channel.

Over the course of time, the treatment tube 234 then becomes filled with tissue fluid by which means the treatment medium present therein, in particular a fluoride-liberating salt, is slowly dissolved.

The release of the treatment medium can also be modified by putting it in resin-bound form into the treatment tube 232, in which case the resin materials are chosen so that the delivery of active substance extends over weeks and months.

If an even more secure sealing of the working channel 32 to the outside is required, it can be countersunk corresponding to the head section 236 of the treatment tube 232, and the head section 236 can be bonded into this countersink.

To remove the treatment tube 232 again, the head section 236 is then drilled out, for which purpose an appropriate drill is placed on the countersink 238.

The treatment tube 232 can also be produced from a tissue-compatible, preferably porous material which remains in the tooth even after the treatment period.

For long-term monitoring and long-term treatment of unexposed lesions it is advantageous to keep the working channel 32 open. For this purpose, a sheathing article 240 can be inserted into the working channel 32 as shown in FIG. 18. This article is a thin-walled glass or metal tube into which tissue cannot grow. A conical head section 242 again ensures a good sealing of the outer end of the working channel 32. The end of the sheathing tube is closed by a screw cap 244. The sheathing tube should be cut to a length such that it terminates before the diseased tissue region 24.

Removal of the screw cap 244 results in long-term access to the diseased tissue region 24. After the treatment is complete, the sheathing tube is withdrawn or remains definitively.

A filling compound is then used to close at least the end of the working channel 32.

Fixed restoration articles for filling the working channel 32 can be precision fit articles, for example made of ceramic or synthetic material (inserts). They close a treated lesion. The sealing is effected with a joining material, for example a cement or a synthetic material for temporary or permanent closure of the working channel.

It is also important in the case of reinfiltration that the working tip 42 sealingly closes the end of the working channel 32 so that the reinfiltration material can be fed under pressure, where appropriate also with exposure to pressure changes or with exposure to sound or ultrasound, into the working channel and fill the defective tissue structure and subsequently the working channel itself too free of bubbles.

After the reinfiltration, the "filling", which occupies the space of the previously diseased dental tissue or the pores or cavities present therein, at least partly and preferably in the region of the cavity edges, consists of a multiphase gradient material comprising in part retained constituents of the dental hard tissue, materials reinfiltrated into the latter, and materials closing cavitations, for example filled synthetic materials.

The principle of reinfiltration and of refilling the defect with a material which is capable of plastic deformation at least for the time for introduction into the defect volume through the working channel, where appropriate with additional use of a packaged precision fit article which is fabricated according to the known shape of the working channel (predetermined by the drill for producing it), for example made of synthetic material or ceramic or metal, takes place by feeding a settable liquid into the working channel 32. The treatment apparatus used for this purpose can have an identical or similar design to the apparatuses shown in FIGS. 4 and 5, it being possible where appropriate to omit those parts of the apparatus which serve to determine the severity and dimensions of the lesion.

FIG. 19 depicts an excavation apparatus which is used for radial widening of a working channel 32 which has been produced by a drill in the region of a lesion which can no longer be healed by remineralization. The excavation tool, which is designated overall by 246, has a hollow-cylindrical tool shaft 248 to the end of which is pivotably attached a flute-shaped cutting tool via a hinge 252. Roughly speaking, the cutting tool has the shape of a semicylindrical flute which is provided on its lengthwise edges with a cutting edge 254. The cutting tool 250 represents, in the resting position shown in FIG. 19, an extension of the lower half of the tool shaft 248 and can be swung out of the clear profile of the tool shaft 248 by a linked actuation rod 256. FIG. 19 depicts the cutting tool 250 in such a swung-out position by broken lines.

Rotation of the tool shaft 248 with the cutting tool 250 increasingly swung out of the resting position results in the cutting edge 254 removing tissue from around the working channel 32. It is possible by simultaneous axial shifting and rotation of the excavation tool 246 to produce recesses in the tissue adjacent to the working channel 32 which have a cylindrical or spherical or other rotationally symmetrical shape. It is possible in this way to remove severely damaged tissue regions adjacent to the working channel 32.

FIG. 20 depicts a modified excavation tool 246 in which the tool shaft 248 is provided with an angled cut 258 to result in a wall section 260 which is curved in the radial direction. A cutting edge 254 is in turn provided on the free end of this section. The wall section 260 is provided with a ramp surface 262 which is impressed radially inward and which cooperates with a cam disk 264 rotatably arranged in the interior of the end of the tool shaft 248. A positioning shaft 266 is fixed to this disk. Two wall sections 260 are preferably provided in the end of the tool shaft 248, symmetrical to the shaft axis, and both are actuated in the same direction by the cam disk 264.

In a resting configuration, the wall sections 260 are again within the clear contour of the tool shaft 248, and they can be progressively extended beyond the outer contour of the tool shaft 248 by rotating the position shaft 266. Tissue regions surrounding the working channel 32 can again be removed by rotating the tool shaft 248, adjusting the cam disk 264 and, where appropriate, axially shifting the tool shaft 248.

In a further modification of an excavation tool as depicted in FIG. 21 at 246, a deformable tubular article 268 is passed through the tool shaft 248. This article is connected to a pressure source 270 as indicated diagrammatically in FIG. 21. The tubular article 268 projects in the axial direction beyond the tool shaft 248 and carries in this region a cutting layer 272 which can be, for example, by a scrim of metal turnings having sharp lengthwise edges. Alternatively, the cutting layer can consist of a metallic rib mesh material or have a layer of particles which provide cutting edges in a geometrically irregular form, for example industrial diamonds.

A cutting layer which consists of a scrim of metal turnings or of a metal lattice such as metal rib mesh may also in addition contain particles which provide irregular cutting edges.

The scrim of metal turnings may also be in such a form that after expansion in the lesion it impresses in the form of a porcupine structure radial porosities into the adjacent tissue material of the lesion, through which it is later possible for treatment materials also to diffuse into tissue volumes which are more remote from the cavity surface and are behind or below the wall surfaces of the cavitation, that is to say into the surface edge structures.

Instead of the tubular article described above, it is also possible for at least the end of the tool shaft to be in the form of a metal pipe, for example made of Nitinol (nickel/titanium alloy).

Nitinol has the property that tools made from it change their shape when the temperature changes (thermally induced expansion). It is thus possible to introduce a pre-cooled and thus collapsed instrument into the working channel, where it is then expanded by warming and displays its geometrically, defined cutting edges or non-geometrically defined cutting edges attached thereto (for example cutting edges of the diamond edging). The withdrawal of the tool from the working channel after the work has been carried out can take place with mechanical compression of the working section by cooperation with the wall of the working channel. Collapsing of this type can be facilitated by the shaping of the tool, for example a frustoconical starting surface of the working section toward the shaft section. It is also possible where appropriate for the tool to be collapsed again by recooling.

The tubular article 268 may also consist of an elastically or plastically deformable material, for example rubber, an elastomeric synthetic material, or else a soft metallic material. In the last-mentioned case, the metallic material which has been widened by application of pressure undergoes plastic deformation again in the radially inward direction when the tool is withdrawn from the working channel and the widened section of the tubular article 268 is withdrawn again from the cavity produced in the working channel 32.

FIG. 22 shows a modified sealing place between a working section 42 of a diagnostic or treatment apparatus and a working channel 32 produced in a tooth. The working section 42 is limited by a conical sealing shoulder 274 at its end remote from the free end. A cylindrical sealing element 276, which may be formed by a piece of silicone tubing, is pushed onto the working section 42. When the working section 42 is moved axially into the working channel 32, the front surface, which is located on the right in FIG. 22, of the sealing element 276 comes into contact with the surface of the tooth 10, which is indicated by broken lines in FIG. 21.

When the working section 42 is pushed further in, the sealing element 276 is moved to the left on the working section 42 in FIG. 22, and its end section remote from the tooth surface slides with radial widening onto the conical sealing shoulder 274, as evident from FIG. 22.

An ultrasonic drilling appliance is designated overall by 278 in FIG. 23 and likewise used to produce a working channel with a small diameter in a tooth.

An ultrasonic generator 282 is arranged in a grip-like housing 280 and operates via a resonance deflector ring 284 on a hollow-cylindrical tool 286.

An abrasive working medium is supplied to the interior of the tool 286 from a pressure pump 288, and this medium may be, for example, an aqueous suspension of abrasive grinding particles as has been illustrated hereinbefore as an example of a treatment liquid. This working medium emerges through the open end of the tool.

The drilling appliance 278 shown in FIG. 23 produces a working channel 32 which has the required dimensions, avoiding additional mechanical tissue damage in the vicinity of the working channel 32. It is also possible thereby to produce non-rotationally symmetrical working channels.

FIGS. 24 and 25 show a further modification of an excavation tool, which is designated overall by 290. It is produced from a cylindrical piece of Nitinol (nickel/titanium material) pipe which is unchanged in a section on the left in FIG. 24 and defines a tool shaft 292, while a front working section 294 has been provided with one [sic] two helical slits offset by 180°. The helical strips 296, 298 remaining between these slits are cut off at the end along a surface line and are sharpened so that an axial cutting edge 300 is obtained there in each case.

Rotation counterclockwise, viewed from the tool shaft, of the excavation tool 290 shown in FIG. 24 results in the cutting ends of the strips 296, 298 running with relatively little resistance over the wall of a previously produced working channel. Rotation of the excavation tool 290 in the opposite direction results in widening in the radial direction of the strips 296, 298 due to the frictional forces and engagement of the cutting edge 300 in each case with tissue material. The cutting edges 300 then detach pieces of tissue from the wall of the working channel. Rotationally symmetrical recesses in the working channel can be made by continuous rotation with the excavation tool 290 shown in FIG. 24.

If the Nitinol pipe is slit only once so that only one helical strip, which has a cutting edge at the free end as described above, is obtained, recesses in tissue regions on one side of the working channel can be made by to and fro movement of the excavation tool.

FIGS. 26 to 29 show plots of pressure changes measured in working channels leading to the diseased tissue region in teeth with damage of varying severity. It is evident from the various measurement diagrams that there are distinct differences in the pressure changes for dental hard tissue with little damage, dental hard tissue with intermediate damage and the possibility of still being healable by remineralization and dental hard tissue with severe damage which can now only be treated by filling.

The working apparatus depicted in FIG. 30 can be used simultaneously for drilling a working channel, for diagnosis and, where appropriate, for treatment.

The working section 42 comprises an outside tubular drilling tool 42a which is mechanically coupled to an ultrasonic transmitter 302 which is fed by a supply unit 304. A guide pipe 42b is arranged inside the tubular drilling tool 42a. This pipe limits, together with the drilling tool 42a, an annular space which is connected to a controllable abrasive material source 306 which may comprise a storage container and a pump for working liquid containing abrasive material.

The abrasive material liquid can emerge through the annular surface between drilling tool 42a and guide pipe 42b and additionally through orifices 308 provided in the outer surface of the drilling tool 42a.

The interior of the guide pipe 42b can be connected via the solenoid valve 62 and the solenoid valve 72 to the suction pump 80 in order to aspirate used working liquid containing abrasive material.

It is evident that the apparatus shown in FIG. 30 can be used to produce well-defined working channels in a tooth by the action of ultrasound (assisted by the abrasive material), but the apparatus can also simultaneously be used routinely for diagnostic purposes and, after completion of the diagnosis, also for treatment.

In a modification, the guide pipe 42b may likewise be coupled to the ultrasonic transmitter 302 or to a separate ultrasonic transmitter (not shown) in order to favor the transport of viscous and/or particle-containing media through the thin guide pipe Itself and/or through the annular space between drilling tool 42a and guide pipe 42b.

In the above description of the diagnostic media and the treatment media, detailed explanations have been given only for those constituents which are particularly important for the functioning. It is self-evident that it is possible in addition to adjust the diagnostic media and the treatment media in respect of their hydrophobic/hydrophilic properties by appropriate additions and, in particular, also in respect of their viscosity. Appropriately inert thickeners are known to the skilled worker.

The invention has been explained above from the view point of medical technology. It appears as follows from the viewpoint of the clinician:

The preferential sites for initial caries lesions are the occlusal fissure relief, the tooth neck region and the approximal surfaces (tooth surfaces in the region of contact with adjacent teeth) of teeth. Compared with the first two preferential sites which are directly accessible to clinical inspection by the dentist, diagnosis of approximal caries lesions by visual (eye) and tactile (probe) means is usually impossible or possible only when the extent is already very large. Diagnosis thereof normally requires intraoral radiographs of the affected teeth.

There are great restrictions on the evaluation of radiographs in relation to unambiguous diagnostic findings or to reproducible decisions about treatment of approximal caries lesions, especially in the case of the smaller or intermediate lesions, because of the extent and the structure of the caries, which is determined by the structure of the teeth and the structure of the dental hard tissue, and the shape of the approximal region: more than 90% by volume of the dental enamel cap consist of mineral calcium phosphate or apatite, a small part of water directly bound to the crystals, and a very small part of <2% by volume of organic tissue. This cap is about 1.0 mm to 1.5 mm thick in the approximal region at the caries preferential site below the equator of the tooth. Adjacent to this into the interior of the tooth, the tooth consists of dentine whose composition is about 45% by volume of mineral material, about 30% by volume of organic tissue and about 25% by volume of water present in dentinal tubules which run predominantly in radial direction.

When X-rays are passed through a tooth from the buccal (X-ray source) to the oral (plane of the film) side, the absorption distances for the radiation energy vary in length from a tangential point absorption to passing through a maximum distance in the region of the middle of tooth. When they pass through dentine regions, they also pass twice (both in the tooth volume facing the radiation source and that facing the film) through the enamel covering on the tooth with more than twice the content of highly absorbing mineral material.

The significance of this for a caries directed toward the middle of the tooth and localized below the approximal contact is as follows: if exclusively melt volumes are affected by the caries, the mineral content of the dental enamel volume with the carious lesion is reduced by comparison with the adjacent healthy dental enamel volume, but not to zero since, because of the prism-like structure of enamel, otherwise the dentine would have had to be reached beforehand. With such an initial caries, the surface of the enamel is, because of its lower solubility, intact in the sense of a permeable membrane for a very long time, underneath which zones of greater decalcification, but with reversible changes in structure, are present. In the X-ray image, in which there is superimposition of the absorption effects along the complete absorption distances (imaging of the bucco-oral third plane on a two-dimensional X-ray image), the differences in absorption caused by the very large differences in the absorption distances are in most cases predominant by comparison with those derived from localized changes in mineral contents in the sense of enamel caries. The result of this physical effect is that reliable radiological diagnosis of selective enamel approximal caries lesions is possible in very few cases.

These blanketing effects which are based on the healthy tooth structure are even more of a problem in the case of dentine caries lesions because healthy dentine has a mineral content of the order of that of tooth enamel with carious lesions, and the mineral gradients caused by the caries are, because of the comparatively low total mineral content of healthy dentine and the superimposition of healthy dentine contents located buccally and orally of the lesion and, in particular, of healthy tooth enamel, the causes of absorption differences which are scarcely radiologically visible. This explains the clinical experience that radiological diagnosis with doubtful reliability is usually possible only with intermediate or larger dentine caries lesions.

Because of the abovementioned structure of an initial caries, in which the mineral content is changed in the sense of a reduced gradient directed from the adjacent healthy dental hard tissues to the center of the lesion, this lesion can, after elimination of the acidic medium caused by bacteria in the direct vicinity of the affected outer surface of the tooth, be remineralized and thus healed. This is relatively simple in the region of the preferential sites of the occlusal fissure relief and of the tooth neck, because of their accessibility and of the surface area thereof, which is comparatively large for a defined lesion volume. Thus, it is unanimously suggested in the modern literature that the therapy variant of first choice is to leave carious tooth neck lesions alone, substantially irrespective of their area dimensions, while simultaneously using modern prophylactic policies. Tooth neck fillings are by comparison exceptionally invasive and characterized by a poor prognosis—indications for tooth neck fillings are mostly based solely on aesthetic demands.

However, it is possible to remove completely the causative plaque in the approximal region only with difficulty and, on the other hand, fluorides which reduce the solubility of mineral dental hard tissue in an acidic medium and shift the physiological de/remineralization equilibrium for the dental hard tissue with the saliva in favor of remineralization, even at pH values below pH 5.5, cannot be administered into the approximal regions or into the lesion volumes either. Stagnation or remineralization of approximal lesions therefore tends to be rare compared with tooth neck lesions.

It is subsequently impossible in most cases to monitor a theoretically desired remineralization clinically, because of the limitations already described for the diagnosis in the accessibility of the approximal region and the radiological diagnosis.

For these reasons, the dentist suspecting a caries lesion must now open up the defect by preparation of a cavity through the occlusal surface in the region of the marginal ridge. Simply to visualize the carious lesion, which is undermined in approximately a pear shape, it is necessary in most cases to sacrifice more healthy dental hard tissue than the volume of the actual caries. The dentist has scarcely any reproducible criteria for the therapeutic decision in favor of preparation of an access cavity, and in many cases he will find a lesion which he could possibly have still remineralized without filling, or an established cavity which has a much larger volume than assumed from the radiological diagnosis.

For the actual mechanical removal of caries, the dentist's criterion is still the surface hardness, although this may show very great inter- and intraindividual variations even in healthy dentine, and is changed in the sense of a three-dimensional gradient structure in dentine with carious lesions. In almost all cases, caries remains histologically after clinical "removal of caries", and many "carious" regions which are similar to the basic structure of dentine with a reduced mineral content, and very probably could have been remineralized, are removed.

The defect produced iatrogenically after visualization and removal of a primary lesion is normally extended further in the region of the cavity edge because of the need to remove undermined areas of tooth enamel which are at risk of breakage but are healthy. In addition, further healthy dentine and enamel volume is removed in order to compensate for the limitations of the conventional and modern filling materials or their processing techniques, for example in relation to minimum layer thicknesses to be complied with, suitable cavity edge angles, elimination of predetermined breaking points or for achieving preset directions of insertion of restorations made in the laboratory etc.

Toward the end of this conventional procedure, a multiple of the original lesion volume in healthy dental hard substance has been sacrificed and replaced by restoration materials which usually have a life of only a few years, rarely a decade. With such restorations it is not uncommon for secondary caries to occur, derived from edge imperfections, which is often even more difficult to diagnose. In a new restoration, usually even more volume of healthy remaining tooth substance is sacrificed, for retention reasons, than in the primary management etc., until scarcely any healthy dental hard substance remains or the pulp of the tooth is irreversibly damaged because of the preparation procedures.

It is crucial for the diagnosis and, where appropriate, treatment of caries to assess its localization and, in particular structure, essentially in relation to the degree of demineralization of the affected dental hard tissue and the possible destruction of organic tissue contents. It is of essential significance to assess the state of the "natural access" (tissue which has become permeable to the surface of the tooth) to the caries lesion according to the abovementioned criteria. The target variable in this case is the ability of aqueous liquids to penetrate through this caries access, because the active lesion is maintained thereby after entry of saliva or bacterial infection, and any remineralization processes must take place through this. Since both the demineralization and remineralization processes derive from diffusion processes determined by concentration gradients, mainly through the caries structures and the cavities caused thereby, the diagnosis according to the invention measures the diffusion variables and the ability of the affected structures to be penetrated. This makes it possible to differentiate between mainly reversible demineralizations with a small proportion of open porosity and substantially intact basic structures or irreversible demineralizations or structural changes with cavitations, which has an essential influence on a causal treatment according to the invention.

When there is clinical or radiological suspicion of approximal caries or caries lesions guaranteed for restoration, according to the invention an iatrogenic access (working channel) with a cross section of about 0.6 mm to 0.8 mm to the lesion is produced in addition to the "natural" caries access. This channel can extend to the center or to the defect edge regions near to or remote from the access. The working channel thus touches the edge of the lesion or penetrates to regions near the center or completely through. It is most favorable to place the access where the distance through healthy dental hard tissue from the outside of the tooth to the presumed center of the defect is kept as short as possible.

Those which have proved suitable besides occlusal accesses, for example starting from a depression in the fissure base of the grinding surface relief, are working channels which originate from the oral surface of the teeth or alternatively in the posterior tooth region from the buccal surface of the teeth, and rarely from the approximal surface (approximal-cervical) of the teeth.

These accesses differ from conventional access cavities in that they do not open up the entire approximal contact region in the form of a box or, not starting from the occlusal surface, take place through the marginal ridge and in particular do not, as is necessary with conventional preparations or else so-called tunnel preparations, include the "natural caries access" in the preparation. This "natural caries access" is thus not mechanically worked, but remains untouched according to the invention, at least before the hydrodynamic diagnosis and, where appropriate, remineralization have taken place.

The working channels can be formed with conventional rotating diamond or hard metal instruments. Oscillating instruments are particularly suitable with the assistance of an abrasive grinding medium which washes round the instruments. It is possible to use solid or hollow tubular preparation instruments. Tubular preparation instruments can be guided considerably more precisely and have the further advantage that tooth material remains in the center of the tube and is available for diagnostic assessments outside the tooth or the oral cavity. For example, this material can be stained with substrate-specific or bacteria-specific staining solutions. A particularly suitable example is a 0.5% strength basic fuchsin solution in propylene glycol for the specific staining of dentine with carious lesions. However, it is also possible to set up bacterial cultures from the removed tissues, which possibly provide evidence for the patient's general risk of caries, or else to undertake histological investigations. This mode of sampling also permits for the first time a monitoring of the caries with high sensitivity and high specificity during recall treatments.

The positioning of the preparation instrument emerges from the angular position of its long axis relative to the tooth form affected and from the presumed center of the lesion. The depth of penetration in the buccal-oral or labial-oral direction likewise emerges from the presumed center and the presumed extent of the lesion, using for orientation the location of the approximal contact, below which the preferential site and the "natural" caries access are located. This relation between clinically visible approximal contact and "natural" caries access is also used for cervical-occlusal estimation of the positional relations between the instrument used to prepare the iatrogenic access cavity and the tooth surface. To simplify the buccal-oral or labial-oral estimation of the depth of penetration, a depth gauge which can be adjusted occlusally extending over the crown of the tooth or on contact with the outer surface of the tooth and which can be displaced approximately parallel to the length of the preparation instrument is attached to the handpiece which carries the preparation instrument. The depth gauge is advantageously fixed to the preparation handpiece by putting a retaining ring which is rotatable somewhat and preferably has an approximately oval shape, on the head of the handpiece. The depth of penetration can then be measured as the difference in the distances which can be read off the depth gauge in relation to a prominent point on the tooth contour or preset in the contact relation, after the preparation instrument has been placed on the outer surface of the tooth and any required point of penetration. In critical cases, it is also possible to take radiographs which are eccentric in relation to the long axis of the tooth or to a buccal-oral plane which runs perpendicular to the dental arch, preferably with a radiopaque preparation instrument adjusted in the defect or analogous instrument gauges, which can also be used for evaluating the positional relation. In most cases it is possible very simply to estimate the position of the instrument during preparations under transmitted light.

The investigation of the working channel produced in this way or, via this, of the lesion can take place in a wide variety of ways. It is possible to inspect the iatrogenic access cavity (working channel), the "natural caries access", any cavities caused by caries or any restoration edge regions, with a light and/or video channel-carrying optical system, it being possible for this endoscope-like video optical system to be both rigid and elastic. Suitable and preferred are lens-carrying optical systems which permit the angle of assessment to be as wide as possible relative to the long axis of the optical portion introduced. However, it is also possible to introduce substrates which selectively mark particular states of tissue (for example caries or destroyed collagen fibers) or bacteria or cavities or particular tissue structures, or are specific markers for particular functional states of these structures, for example in relation to the diffusion ability or the bacterial vitality or in respect of metabolic activities or tissue vitality or mortality, into the defect via the working channel. Possible examples of such substrates are dyes or X-ray contrast agents or ultrasonic contrast agents or infrared or ultraviolet contrast agents or light wavelength-specific contrast agents or fluorescent substrates or their precursors (which become fluorescent dyes through the metabolic activity of the bacteria) or contrast agents for characteristic frequency analysis or radio nucleides [sic] etc. These may also be identical to a provisional or definitive filler which is to be introduced into the cavity or to another therapeutic or diagnostic agent, or be present in the latter. It is possible in this way to compensate partly or substantially for the disadvantages of the X-ray investigation described at the outset in relation to the absorption characteristics of dental hard tissue with carious lesions, or metric evaluations are possible, or assignments to structural features, for example porosities, are possible, or the differentiation of structural features or functional states are [sic] possible depending on the arrangement of selective, for example hydrophilic or hydrophobic carrier substances for these substrates, or tomograms of the defect can be obtained, or films can be made in unusual, for example arranged perpendicular to the long axis of the tooth, occlusal-cervical (oblique) planes, or other diagnostic methods can be employed. It is very particularly advantageous in this connection that it is possible to dispense with X-rays, for example in favor of transillumination with visible light, ultraviolet light, infrared light or laser light. In a further modification, light frequency filters suited from this light for the marker substrates or their metabolic products (for example due to bacterial metabolism) and/or correlating observation filters are used. This may make it possible for the observer more easily to identify light or fluorescent effects with comparatively weak light. It is also possible in many cases to determine more accurately the size or structure of the defect depending on the capacity of the standardized iatrogenic access cavity, and of the lesion.

The above substrates may react in an acid-base reaction simultaneously with the, in some cases acidic, medium inside the cavity volume, possibly neutralize this medium and thus temporarily restrict the precondition for progression of caries and/or form a salt which blocks the porosities or, in some cases, the cavities or, in particular, the diffusion cross sections.

It is further possible to select, for example, tissue-specific or structure-specific or surface-specific or metabolism-specific or bacteria-specific substrates so that they preferentially adhere to these tissues, structures, surfaces or bacteria, or accumulate in them. It is possible by suitable choice of these substrates according to the required effect or the required addition or incorporation or by chemical combining of these substrates with osmotically or chemically active substances or selectively energy-absorbing substances for these tissues, structures, surfaces and bacteria to be marked and, for example, to be, preferably selectively, destroyed by water which has accumulated due to osmosis (bursting of bacteria) or by chemical reaction with a reagent introduced via the working channel (for example by specifically induced gas formation inside bacteria) or by selective energy absorption, for example of high-energy radiation (for example light) or mechanical (for example ultrasonic vibrations), thermal etc. energy.

It is, of course, also possible for such substrates to be employed for the initial diagnosis of a tooth not yet provided with a working channel in order, for example, in addition to a conventional clinical or radiological diagnosis to elucidate the integrity of a carious approximal tooth surface in question and any need for further diagnosis via a working channel.

It is also possible to measure more accurately the sensitivity (reaction to thermal stimuli) or the vitality of the crown pulp (for example laser Doppler interferometry) and, where appropriate, in the case of multirooted teeth, of the root pulp by means of one or more working channels due to the reduced dental hard substance layer thickness between the internal surfaces of the working channel and the pulp cavity. Several working channels to a suspected lesion are also possible for any other reason than for determining the pulp sensitivity or vitality, for example for reasons of simpler diagnosis, more favorable remineralization or simpler reinfiltration.

Further diagnostic evidence is provided by the electrical resistance measurement, which is possible for the first time, between the approximal lesion and a skin electrode. The measuring probe which is advanced stepwise through the working channel has a tubular cross section with a central measuring probe which is continuously flushed by air on all sides. This method, which has to date been confined to the fissure region, is exceptionally sensitive and provides for the first time reproducible measurements which can be used for diagnosing the progress of caries and which can form the basis for a reliable decision about treatment.

However, the greatest sensitivity and specificity in the differential diagnosis or diagnosis of the progress of approximal caries lesions is achieved by the "hydrodynamic diagnostic method" according to the invention:

As stated above, it is possible to differentiate between predominantly reversible demineralizations with a small amount of open porosity and substantially intact basic structures or irreversible demineralizations or structural changes with cavitations by introducing an approximately cylindrical tube into the working channel and sealing, for example, by clamping a section of silicone tubing between the outer tooth surface and the tube which is, for example, conically divergent outside the access, or placing the tube, preferably via sealing lips, from outside on or over the iatrogenic access. This tube is preferably an exchangeable component of a handpiece and is inclined at an angle different from 0° or 180° C., particularly suitably about 60°, to the long axis of the handpiece. It is possible to use tubes which are at least partly, plastically or elastically deformable. A liquid, a gel or a paste or a gas is then introduced via the feed lines in the handpiece or the relevant infrastructure of the apparatus and via the access into the defect and, depending on the structures present and on the structures in the region of the "natural access", where appropriate, subjected to pressure, which can be measured by using suitable pressure sensors and computer-assisted data analysis. It is also possible on the other hand to apply a defined closed vacuum over the tube and measure the time course of a vacuum which is effectively produced. The level of this closed vacuum is limited by the potential risk of aspiration of odontoblasts on the inside of the predentine layer in the pulp cavity into the adjacent dentinal tubules. These maximum levels of vacuum vary greatly depending on the condition and structure of the dentine and on the dentine layer thickness, which can scarcely be measured, between the lesion and underlying pulp cavity. Suitable maximum pressure reductions have been found to be <800 mbar, in particular <300 mbar, in particular <100 mbar.

There is a significant build-up of a pressure or vacuum gradient, or the capacity is limited, only if the "natural" caries access has a negligible structural incursion. Lesions of this type can be induced to stagnate or induced to remineralize after cleaning the tooth surfaces, where appropriate disinfecting the working channel and, where appropriate, lesion portions, and, for example, by assistance by means of fluoride application or with use of fluoride products modified by additions of calcium or phosphates.

As an alternative to this, the tube, for example a metal tube or a plastic tube or a glass tube or a ceramic tube or a tube made of any other material, for example a polymer ceramic or a non-circular tubular structure of these materials, can be permanently bonded or cemented, for example, into the iatrogenic access, which seals the ground tooth surfaces and seals the joint regions. In addition, the definable inlet geometry of this, for example, tubular structure which is bonded into the tooth simplifies, where appropriate with the assistance of a possible packaged sealing ring, the tight connection of the filling tube or the like of the handpiece. It is important that in this case a releasable but tight connection between the struture bonded into the tooth and the structure fastened to the handpiece can be produced (sealing ring, drawn-over tubing, sealing lip etc.).

The introduced liquids are not compressible and can be very easily adjusted or preselected in terms of hydrophobicity (for example silicone oil) or hydrophilicity (for example water). It is also possible to prepare solutions, suspensions, emulsions or dispersions or even particle-filled (for example aqueous microdisperse thixotropic silicon dioxide or aluminum oxide dispersions) or non-particle-filled gels, which can likewise be introduced into the cavity. Under varying positive pressure conditions, any build-up up of positive pressure occurring (0.1 to 8 bar, preferably 0.1 to 5 bar) is measured and/or a defined amount flowing through is measured with the abovementioned application of pressure and/or a passage through the natural carious access is recorded, where appropriate with the assistance of the above-mentioned marker substrates, for example dyes etc. An induced remineralization can be attempted with positive pressure changes >2 bar which can be built up via the working channel, for example using aqueous solutions, or with a leakage of these aqueous solutions through the "natural" caries access of less than 0.1 mm/20 s (with a pressure difference of +2 bar) or with precluded visible leakage of the marker substrates or other carrier materials through the "natural" caries access, for example into the approximal space. These substrates or dyes may simultaneously be adhesives (for example solutions containing carboxyl groups, modified polyacrylic acid solutions, solution mixtures containing acrylate mono- or polymers or solvent- (for example acetone-) containing acrylate monomer solutions or polymer solutions etc.) or etching solutions (for example organic or inorganic acid solutions) or disinfectant solutions (for example chlorhexidine solutions) or acid-neutralizing solutions which simultaneously condition the dentine or the enamel in the sense of chemical restructuring of the tissue surfaces.

It has proved suitable in practice for the filling tube not to be placed as far as the base of the iatrogenic access or its orifice not just to be formed frontally or laterally, but for the two orifices to be combined or for inclined frontal orifices to be formed in relation to the long axis of the tube.

As an alternative to the pressure gradients it is also possible to investigate the amount flowing through when a pressure is applied (migration of air bubbles with a defined tubular access=known volume increment).

As an alternative to pressure gradients or together with the latter, any vacuum which can be built up in the lesion and its behavior over time under defined suction powers is assessed.

It is thus possible for the first time to assess the "natural" caries access in relation to its structure, its diffusion variables and thus to its remineralization potential in the sense of the healing of caries which may be possible.

It is possible and preferable not only for the liquid to be introduced from a connected storage container through the filling tube in to the iatrogenic access and thus into the lesion; on the contrary, it can be aspirated through the same access, preferably through the same tube, into another disposal container or into an attached dental aspiration device. This facilitates inspection of a defect before its diagnostic assessment by video analysis, pressure gradients etc.

It is also possible therewith to carry out pressure/suction alternating cycles in the sense of a pumping effect with, for example, regular or irregular irrigation (pressure) or suction cycles, by which means debris, where appropriate dissolved hard substance precipitates and organic tissues which have been partly or substantially or completely destroyed in structure, or tissue residues or bacteria etc. are eliminated from the defect (=hydrodynamic preparation). It is possible by these alternating cycles to destroy bacterial cell walls or producing cavitation effects acting where appropriate to ablate hard substance.

It is further preferred to employ solutions or solution mixtures suitable for dissolving demineralized tissue residues or destroyed organic tissue residues, for example aqueous sodium hypochloride [sic] solutions in concentrations below 6%, preferably below 3%, particularly preferably around 1% and/or aqueous calcium chelating agents, for example EDTA solutions below 50%, preferably around 20%, and/or N-monochloro-DL- 2-aminobutyrate-containing solutions and/or amino acid-containing solutions. These or the above-mentioned active substances (marker substrates, dyes, substances for enamel or dentine conditioning) can be mixed into the storage container, or different storage containers with changeover devices can be used, or concentrated solutions can be attached in defined mixing ratios, for example in cartridge form, in the handpiece or elsewhere, and be mixed with the liquid fed from the storage container (s). It is also possible for the tube simultaneously to be designed as (preferably disposable) storage container for particular liquids, in which case the expulsion of this liquid takes place indirectly via the air pressure or liquid pressure which can be built up in the handpiece, for example via a plunger in the tube. This principle is particularly suitable for the infiltration of, for example, setting filling materials within the framework of the abovementioned reinfiltration, because it is possible in this way to avoid cleaning problems in the handpiece. It has further proved suitable also to convey gases through the same filling tube of the handpiece, essentially compressed air of dental quality, for drying the access cavities or the defect. However, this can also take place with a separate source and a separate filling tube which is attached, for example, to conventional dental compressed air sources.

Where the hydrodynamic (pressure build-up, vacuum build-up, time courses of pressure and vacuum, defined, substantially finite capacities, fluid-dynamic resistances) and/or where appropriate for assistance the chemical (hydrophilic or hydrophobic liquids or gels or structure-sensitive or structure-specific or tissue-sensitive or tissue-specific marker substrates and/or contrast agents etc.) and/or the physical (for example electrical resistance or impedance measurement) and/or the optical (endoscopic) diagnosis reveals the possibility for an induced remineralization, where appropriate assisted by therapeutic measures, the procedure is as follows:

Several hydrodynamic measurements are carried out during the increasing penetration forming part of the preparation of the working channel, especially after the enamel cap has been drilled through, until the defect is touched or penetrated. Two to three measurements usually suffice to carry out an individual defect-specific calibration, the values of which can then be examined for significances, or this is recognized in most cases very simply because, for example, no further pressure build-up is possible after a particular penetration into the defect if its "natural" access has undergone severe structural changes and no longer represents a diffusion barrier. Such values can also be used in part for a plurality of lesions to be treated, in treatment sessions which are not several years apart, on a patient for assessing other teeth in this dentition.

Where the hydrodynamic diagnosis with liquid columns reveals a finite capacity compared with that due to the tight closure of the iatrogenic access of the defect with a significant rise in pressure, or the capacity scarcely increases over a defined period of, for example, less than 1 min, the structure of the caries is probably characterized predominantly by mineralization gradients with structural features which are not fundamentally changed by comparison with intact dental hard tissues, in particular ally [sic] changed structural features, in particular with substantially intact organic structures; it is possible that the enamel surface is provided only in the form of a membrane-like, substantially closed surface layer, and the defect can thus very probably be remineralized.

As an alternative to the handpiece described, it is also possible to use, for example, syringe-like instruments which can be operated manually, in which case the expelled volume is recorded and the pressure difference is relieved manually, or the pathway difference of a moved air-bubble in, for example, a cylindrical cross section is measured.

For investigating pressure maxima, it is necessary where appropriate for the "natural defect access" to be superficially cleaned or, for example, be separated by introducing a wooden wedge from the approximal surface of the adjacent tooth. In this case, the use of an etching solution for investigating pressure gradients makes it possible to condition the defect-forming demineralized dental hard tissue or the adjacent intact dental hard tissue and thus provides an improved diffusion cross section for diffusioning of saliva and, for example, therapeutic active substances such as, for example, the fluoride products normally used in dentistry. However, it is also possible to use adhesives which influence the quality of the diffusion barrier, for example by blocking porosities. At the same time, the bacteria localized in the defect and, where appropriate, smear layers are respectively effectively killed and removed. It is obvious to record the pressures and, where appropriate, liquid capacities and/or the endoscopic images and/or other findings in order to have comparison quantities during the monitoring in the course of checking the success of the remineralization treatment or, where appropriate, induced remineralization, and thus to identify trends in the re- or further demineralization reproducibly, preferably without any further X-ray image.

After irrigation or aspiration and, where appropriate, drying of the iatrogenic access cavity and, where appropriate, adjacent defect volumes, preferably a tube made of the abovementioned materials is inserted into the defect in such a way that the center of the lesion is connected by the tube to the tooth surface. This tube moreover seals the healthy dental hard substance surfaces which have been cut into during the preparation of the iatrogenic access. It is advisable before inserting the tube for the dental enamel surfaces adjacent to the latter to be restructured in a microretentive manner by acid etching and for the outer tube surfaces to be prepared by acid etching or another type of pretreatment, for example silicatization, for a bond, where appropriate with additional use of adhesion promoters such as, for example, silanes, with a joining polymer composite with which the tube is adhesively inserted into the iatrogenic access cavity. Any projections of the tube beyond the outer tooth surface are preferably removed. However, the definitive or temporary introduction of a tube is normally dispensed with, and the working channel is used directly. First of all, a fluoride product which is preferably modified by calcium or 9 phosphate additions is introduced, for example by means of a tube, under positive pressure into the defect and, where appropriate, the access cavity. Aqueous fluoride solutions are preferably used and are left in the abovementioned region under pressure for a certain time. The pressure is preferably set at above the pressure maximum used for the diagnosis in order thus to perfuse fluorides into the volume of the lesion via forced diffusion into the water present or bound in the changed dental hard tissues in each case. It is further possible to introduce, before or with or after the introduction of these solutions, solutions, gels or (for example solvent-containing) lacquers which reduce the adhesion of plaque (for example delmopinol solution, triclosan solutions, solution mixtures) or impair the vitality or the metabolic activities of plaque, via the working channel into the volume of the lesion and/or the "natural defect access" and/or the working channel.

At the same time, the plaque on the corresponding tooth surface is removed by supra- and subgingival tooth cleaning, any retention niches or approximal plaque are eliminated and the patient is instructed concerning individual oral hygiene procedures. Finally, if a tube has not yet been bonded in the access as stated above, such a tube is now bonded in for sealing, and the tube or, if one has not been introduced, the working channel is closed with a plastic and preferably setting or settable material(s) which is as easy to remove as possible but nevertheless as bacteria-tight as possible, such as, for example, plaster, synthetic material, silicone, polymer composite, composite materials etc. or with use of geometrically defined, for example stopper-like, molded articles or combinations of molded articles and plastic materials. A provisional closure can also be effected with active substance-, for example fluoride- or chlorhexidine-releasing closure materials in the sense of a depot.

Where tubes are introduced, these can be reversibly closed at the end penetrating the outer tooth surface also with a closure mechanism, for example an internal thread with corresponding self-sealing screw or with use of additional seals.

An external conventional chlorhexidine or fluoride application with chlorhexidine or fluoride liquors which adhere to the dental hard substances or to the closure of the iatrogenic access or in the region of the "natural" caries access is additionally advisable in some circumstances.

This closure can be reopened after a period which is determined by the individual caries risk and the oral hygiene of the patient and is from a few weeks to a few months, and the defect can be reevaluated in analogy to the initial diagnosis. The assessment is based on the same criteria as initially, it now being possible to use the baseline data from the initial treatment for comparison. The active substance, for example fluoride treatment should be repeated where appropriate. If, however, it no longer appears possible to induce remineralization, the defect can be reinfiltrated through the same access without further preparative measures. It is, of course, possible at any time to treat with conventional filling procedures without disadvantages. Thus, in cases of doubt about possible remineralization or where reinfiltration is already necessary it is possible firstly to attempt remineralization in many cases.

Depending on the individual situation, it is advantageous for optimization of the remineralization for certain periods not to close temporarily the orifice of the iatrogenic access or of the tube bonded in, in order to allow adequate entry of saliva. In this case, however, the access should be cleaned, preferably each day, for example using compatible brushes or by irrigations, and the growth of vital bacteria should be prevented by regular use of chemical active substances, for example of chlorhexidine or the abovementioned antiadhesives etc.

If it is not possible, despite sealing of the iatrogenic access, for a pressure gradient to be built up, or if the introduced solution flows out again to the "natural" carious access, the defect is prepared by irrigations or suction procedures or irrigation/suction alternating pump procedures, where appropriate with the assistance of solutions assisting dissolving or ablation, or etching solutions (hydrodynamic preparation). Such solutions or mixtures of various solutions can make possible or assist in particular the, where appropriate selective, ablation of organic dental tissues damaged in their structural tissue residues (for example sodium hypochloride [sic] solutions etc.) or of highly decalcified hard substance volumes (for example EDTA solutions, inorganic or organic acid solutions). To generate more efficient pressure/suction waves, the "natural defect access" can be temporarily closed for example by attaching a matrix band, or, conversely, the "natural defect access" can be lifted off the adjacent tooth surface and thus opened where appropriate by separation of the adjacent teeth, for example by introducing a wedge into the interdental space region. Wedges introduced into the affected interdental spaces, for example wooden wedges etc., also help to avoid aspiration of soft tissue or entry of blood, for example from the interdental gingival papilla, during the treatment. The deaeration of the defect structures on introduction of active substances takes place via the "natural defect access". It is possible to check the states of the defects and progess in treatment at any time by an endoscopic examination or by introducing specific or structure-sensitive marker substances. After hydrodynamic and/or chemical and/or where appropriate assisting mechanical (for example using endoscope-like micromechanical instruments which are advanced via the working channel into the defect and have geometrically defined or undefined cutting edges, for example balloon-like instruments which have cutting edges and can expand in the defect volume due to entry of liquid) preparation of the defect, the surfaces adjoining the defect are restructured and conditioned (priming) for example by etching solutions such as, for example, acidic aqueous solutions. During this, any applied reduction in pressure (vacuum) must not exceed a critical size of about 800 mbar in order to avoid any aspirations of the odontoblast layer which adjoins the predentine zone within the pulp cavity.

It is further possible for the solutions used for the hydrodynamic preparation, for example for the rough depuration of the defect or for its assisting mechanical preparation, additionally to be mixed with particles such as, for example, glass particles, calcium phosphate particles, hydroxyapatite or fluoro-apatite particles, calcium fluoride particles, salt particles, carbonate particles, fluorspar particles, ceramic particles, synthetic material particles or composite particles with an average particle size of <100 $\mu$m, preferably <50 $\mu$m, essentially preferably <20 $\mu$m and very preferably <10 $\mu$m, in the liquid which acts on or infiltrates into the corresponding surfaces, in the sense of a suspension or dispersion, in order to assist or expedite this process by additionally result-ing micromechanical preparation measures or erosion effects.

It is subsequently possible for the defect-forming volumes and their adjacent structures to be dried with compressed air if necessary.

If necessary, the neighboring tooth surface is isolated to protect it from contamination through the "natural access", for example by introducing a separating strip (for example acetate strip) or, for example, a matrix into the relevant interdental space region. This is followed by reinfiltration of the defect-limiting structures (bridging) and of the actual defect volumes (refilling) by introducing suitable adhesives and/or filling materials through the iatrogenic access (working channel) until the "natural" and the iatrogenic access is closed. During the reinfiltration and the refilling, any residual volumes of liquids, and air, present in these structures are pushed in front of the reinfiltrated material and expelled through the "natural access"; excesses of reinfiltrated material can very easily be removed following the affected approximal tooth contour.

The interpenetration of hydrophobic filling material in particular permits, in the case of directed flow, this material to push the liquid in front of itself, and aqueous liquids or, where appropriate, excesses of lower viscosity infiltration materials or adhesives, if these do not directly wet the surfaces to be reinfiltrated, are expelled through the natural caries access. Suitable reinfiltration or filling materials are all plastic and setting or settable materials which can be introduced through such access cavities, in particular thixotropic materials, preferably synthetic materials, monomers, polymers or particle-filled polymer composites, such as, for example, acrylate plastics or organosilicon materials, or compomers or cements such as, for example, glass ionomer cements etc. In some circumstances, different types of materials with, where appropriate, different hydrophilic or hydrophobic properties, different viscosity and different degree of filling are introduced, preferably successively. Combinations of reinfiltration materials or filling materials with primer substances and/or the abovementioned active substances such as, for example, chorhexidine or fluorides etc. are also possible. Last but not least, also suitable for the reinfiltration are resins dissolved in solvents, for example acetone, in particular polymer resins or partially filled polymer resins.

The structure forming the caries volume, or these structures, may not in this case necessarily be removed completely in the conventional mechanical sense; on the contrary, they form a type of sponge structure which is (re) infiltrated in the sense of a guide structure for the materials to be introduced, and thus remain as framework of the supply. At the same time, this interfacial penetration results in gradient structures which are favorable for mechanical loads and is the morphological substrate of fine interfacial adhesions.

At least the high quality of an adhesively anchored composite filling is achieved in the region of the "natural" and the iatrogenic access cavity, with the small volumes of reinfiltrated material having a beneficial effect on the residual tensions which are intrinsic to the material and are frequently induced during the phase change of the filling materials, and thus have a quality-increasing effect.

Where vital bacteria are still present where appropriate in the reinfiltrated or refilled original defect volumes, these are eliminated with the directed inflow either through the "natural access" or integrated as component into the interfacial structures or the filling, after which they have no chance of survival, because of the isolation of substrate, and are also unable to carry out any degradative metabolic activities.

A directed flow of the material during the reinfiltration or the refilling can be additionally improved by applying to the affected approximal region an additional vacuum cup which is partly or completely sealed toward this spase, for example by sealing lips.

After complete reinfiltration of the surfaces adjoining the defect or after filling of the original defect of the "natural" access and of the working channel, and the removal of any excesses from the approximal region, these surfaces are smoothed and the reinfiltrated material undergoes photo-catalytic setting. It is, of course, also possible to use, for example, autocatalytic, dual catalytic thermosets or, for example, melt-processible polymer matrices.

When the filling volumes are larger, the defect can also be filled in layers, starting from the original "carious" access until the working channel is definitively closed, in which case the initial volumes of reinfiltrated or filled material are, where photo-catalytically polymerizable polymer systems have been used at least in part, polymerized additionally or exclusively with light probes introduced via the iatrogenic access into the defect and/or transdentally. Subsequent work is unnecessary in most cases.

In the case of defects near the pulp, it is also possible to infiltrate substances acting on the pulp by the possible application of pressure, such as, for example, bone morphogenetic proteins (BMP) or aqueous calcium hydroxide solutions, to induce hard tissue formation, or potassium or strontium solutions, for example for reducing the sensitivity of the tooth.

Essential advantages compared with conventional filling techniques are the substantially pain-free preparation, a considerable sparing of healthy dental hard tissue, a considerable simplification in the usual adhesive technique working steps, for example by possible dispensing with a rubber dam, a higher quality of the adhesive bacteria-tight closure, a possible therapeutically utilizable infiltration of active substances which can be controlled by pressure gradients, for example against the peripheral outflow of liquid from the dentinal tubules.

Appropriate for the preparation instruments initially used for preparation of the iatrogenic access, these can simultaneously be used either as cylindrical tubes to be introduced temporarily or definitively into the defect or full-volume precision fit articles, or such tubes or fitting articles can be provided in the same shape made of suitable materials such as, for example, metals, ceramics, synthetic materials or composite materials, for example in a kit, and be used to close the access cavity by using the reinfiltrated filled material in the sense of joining materials.

Hydrodynamic or chemical diagnostic methods and instruments of these types can also be used for the diagnosis of sensitive tooth surfaces in the region of the tooth neck and for differentiation of particularly critical surface areas on a region of a tooth neck, for example via in the sense of suction cup-like instruments with circular sealing lips, preferably in various size gradations. It is then possible, in the same course as the diagnosis, to carry out, very simply and comparatively very effectively, controlled pressure infiltrations of substrates which reduce the sensitivity such as, for example, aqueous potassium or strontium solutions.

It is also possible to mechanically block, at least partly, in the sense of reducing the diffusion cross section, the superficial, partly opened dentinal tubules by adding particles such as, for example, glass particles, calcium phosphate particles, hydroxyapatite or fluorapatite particles, calcium fluoride particles, ceramic particles, synthetic material particles or composite particles with an average particle size of $<50\,\mu m$, preferably of $<20\,\mu m$, essentially preferably of $<10\,\mu m$ and very particularly preferably of $<2\,\mu m$, to the liquid to be applied to or infiltrated into the corresponding surfaces—in the sense of a suspension or dispersion.

It is furthermore possible to admix to the solutions in this use other active substances which, for example, impair plaque vitality or the plaque adsorption characteristics or promote remineralization, such as, for example, chlorhexidine or fluorides etc. (see detailed list of active substances above).

Further possible uses exist in connection with the sealing of fissures in teeth or dentures. For this purpose, the fissure flank surfaces are preferably conditioned hydrodynamically and the fissures are then reinfiltrated at least partly in the sense of a "hydro-dynamic" adhesive sealing.

The described device and the described methods also function in the same sense in the case of existing dentures. Where these are made of metal, a radiological investigation for possible secondary caries is impossible because of the absorption of X-rays in the restoration. To assess the quality of the restoration and of the tooth surfaces adjoining this, especially in the edge region thereof, a tubular iatrogenic access (working channel) is prepared to penetrate the restoration at the site in question. This is followed by a hydrodynamic or chemical diagnosis and/or a treatment, for example in the sense of a hydrodynamic or chemical or micromechanical preparation of the defects, with subsequent reinfiltration and temporary or definitive closure of iatrogenic access. The possibility for conventional replacement of the restoration, as part of a conventional production of a new restoration, is not ruled out.

Description of a Course of Treatment:

The description of the expedient procedure for diagnosis and treatment when approximal caries is suspected takes place in accordance with a flow diagram as shown in FIG. 31.

A suspicion of approximal lesions normally arises during a routine dental examination, rarely clinically, as a rule after radiological examination. If the lesion is already so large that there are incursions on occlusal tooth surfaces or another large-area occlusal access exists, for example in an insufficient primary filling, the diagnosis is usually not a problem, and a conventional filling treatment is performed.

In the other cases, the X-ray image provides in some circumstances information about whether and how far the dentine volumes are affected by the lesion. IT is the dentist's duty to decide on the basis of a large number of assessable criteria relating to the patient, his dentition situation, his caries risk, his oral hygiene, his compliance etc., whether the defect should be monitored for a certain period by conventional methods and in connection with conventional prophylaxis, or whether, as will be necessary in the majority of cases because of the limitations described at the outset in the conventional diagnostic methods, it is necessary to carry out further diagnosis and, where appropriate, treatment according to the invention.

In accordance with the indication described above, a tubular access cavity is prepared according to the invention so as to produce a working channel to the defect which is as short as possible, spares dental hard substances, can easily be reached, is not aesthetically unpleasant and can be closed again simply and in a bacteria-tight manner, and is preferably not located in a zone of high occlusal chewing stress.

This is followed by a brief rinsing through, where appropriate with rinsing round instruments which are oscillating in the sonic or ultrasonic region and have been introduced into the working channel, aspiration or suction/pressure irrigation and, where appropriate, drying of the defect and of the working channel and a possible endoscopic inspection. After this, the handpiece is provided with a tube, the latter is inserted into the working channel and sealed in order to assess the structure of the lesion, and the diffusion variables and/or the permeability of the "natural caries access", by means of hydrodynamic and/or chemical diagnosis (marker substrates).

If there are reversible changes in the lesion-forming structures and low permeability of the "natural access", it is advisable to introduce adhesively an access tube into the iatrogenic access, which can thus be closed obviously tightly. This means that all the tooth surfaces cut into in the preparation are permanently sealed, and the defect has a permanent access which can be used for treatment.

The data obtained in the diagnosis are documented as subsequent control variables. Then an aqueous fluoride product is perfused into the lesion via the working channel, and the pressure necessary for this is, where appropriate, maintained for a period, or water-soluble depot fluoride substrates are slowly introduced, for example, and the access is then closed in a bacteria-tight manner.

This is followed by conventional prophylactic measures and, after a certain time, reevaluation of the lesion by the same procedure using the working channel, with the data acquired in the original diagnosis being used as comparative variables to estimate the success of the treatment. The treatment is repeated where appropriate.

If irreversible structural damage in the region of the lesion or high permeability or unrestricted diffusion through the "natural caries access" is initially diagnosed or emerges during the course of control investigations after induced remineralization, the defect is prepared with hydrodynamic and/or chemical and/or micromechanical and/or mechanical assistance and/or by the action of instruments rinsed round with fluid or abrasive and oscillating in the sonic or ultrasonic region, where appropriate with central aspiration through the instrument, and the defect-limiting surfaces are subsequently conditioned in the sense of priming. Endoscopic control is possible regularly and facilitates the control of these preparation measures.

Subsequently, the defect-limiting structures and the defect itself are reinfiltrated (bridging) or filled (refilling), where appropriate in several stages. This is followed by conventional prophylactic measures and conventional follow-up investigations. It is, of course, possible if ever necessary to introduce conventional dental fillings into the affected tooth surfaces at any time without any additional damage caused by the treatments according to the invention.

What is claimed is:

1. Apparatus for determining the remineralization ability of a hard tissue with a measuring device (46, 60, 86, 88; 104, 114, 116, 86, 88; 130–140, 88; 144–148, 88; 150–154, 88; 156, 86, 88; 158–174) for local measurement of a physical property of the hard tissue,
characterized in that
the measuring device has a measuring head (40) with a rod-like probe section (42), which probe section (42) is introducible into a working channel (32) of the hard tissue and comprises a measuring element (46, 60; 104, 116; 130, 134, 138; 144, 148; 150–154) being connected to the probe section (42) and responding to the physical property of porosity of the hard tissue, the measuring head (40) has a sealing element (54) which cooperates with a section of the tissue surface, and the measuring head (40) is connected to a fluid source (76; 80) which is under a pressure different from normal pressure, and the measuring device measures the fluid leakage through the tissue to be investigated.

2. Apparatus according to claim 1, characterized by a position indicator (48–52) for the axial position of the probe section (42) in relation to a contour surface of the tissue.

3. Apparatus according to claim 2, characterized in that the probe position indicator (48–52) has an input part (48) which cooperates with the tissue surface and which is arranged axially displaceably on the probe section (42) and is supported by a spring (50) on a stationary apparatus section, which spring (50) acts on a force sensor or deformation sensor (52;1).

4. Apparatus according to claim 3, characterized by an evaluation unit (88) which receives the output signals of the probe position indicator (48–52) and the output signals of the measuring element, and compares the output signals from the latter, which are obtained when the positions of the probe section (42) differs with one another, for which purpose the signals obtained for each of the different probe positions are stored as a function of the output signals from the probe position indicator (48–52).

5. Apparatus according to claim 1, where the measuring element has a radial measuring axis, relative to the axis of the probe section (42), characterized in that the probe section (42), is arranged rotatably (118–122) on the measuring head (40).

6. Apparatus according to claim 1, characterized in that the measuring head (40) is attached to a grip part (36) having a long axis.

7. Apparatus according to claim 6, characterized in that the long axis of the grip part (36) and the axis of the measuring head (40) are inclined with respect to one another.

8. Apparatus according to claim 7, characterized in that the long axis of the grip part (36) and axis of the measuring head (40) are inclined at an angle between about 30° and about 90°.

9. Apparatus according to claim 7, characterized in that the long axis of the grip part (36) and the axis of the measuring head (40) are inclined at an angle of about 60°.

10. Apparatus according to claim 6, characterized in that the grip part (36) is connected via a rotating joint (99) to a supply cable (101).

11. Apparatus according to claim 6, characterized in that the grip part (36) having a long axis is rotatable about said long axis.

12. Apparatus according to claim 1, characterized in that the measuring device has a first sensor part (104; 130, 138; 144; 150–54; 158, 160) acting on the tissue to produce a stimulus and a second sensor part (116; 130, 134; 148; 150–154; 164–170) measuring the response of the tissue to the stimulus, and in that means for adjusting the strength of the action produced by the first sensor part are provided.

13. Apparatus according to claim 12, characterized in that the adjusting means comprise an input device (94) carried by a grip part (36).

14. Apparatus according to claim 12, characterized in that the adjusting means comprise a program control (88).

15. Apparatus according to claim 14, characterized in that the program control operates so that the first sensor part (104; 130, 138; 144; 150–54; 158, 160) is stimulated so that a preset output signal is obtained at the second sensor part (116; 130, 134; 148; 150–154; 164–170).

16. Apparatus according to claim 1, characterized in that the fluid is a gas and in that the measuring head (40) is connected via an on-off valve (62) which has a closed position to a fluid source (76; 80), and a pressure gauge (60) is connected to the measuring chamber which is limited by the measuring head (40) and the pressure gauge is adapted to be limited by the tissue.

17. Apparatus according to claim 16, characterized in that the measuring head (40) has a pressure reservoir (58) connected to the measuring chamber.

18. Apparatus according to claim 1, characterized in that the diagnostic fluid is a liquid and in that a flow meter (66) is arranged in the supply line leading from the fluid source (76) to the measuring head (40).

19. Apparatus according to claim 18, characterized in that the flow meter (66) has a capillary tube and means for feeding gas bubbles into the downstream end of the capillary tube.

20. Apparatus according to claim 1, characterized in that the sealing element (54) is carried by a free front surface of the input part (48) of a probe position indicator (48–52).

21. Apparatus according to claim 1, characterized in that the probe section (42) is a cylindrical pipe which is closed at an end (44) and which has at least one fluid emergence orifice in its peripheral wall.

22. Apparatus according to claim 21, characterized in that the probe section (42) has at its end next to a grip part (36) a shoulder (274) which expands in the radial direction, and in that a sealing tube (276) is arranged on the outside of the probe section (42) and is widened when pushed with its end which is next to the grip part (36) of the probe section (42) onto the sealing shoulder (274).

23. Apparatus according to claim 21, characterized in that the shoulder (274) is conical.

24. Apparatus according to claim 1, characterized in that the measuring head (40) can be connected by a reversing valve (72) alternately to a positive pressure fluid source (76) and a negative pressure fluid source (80).

25. Apparatus according to claim 24, characterized by means (102) for collecting the liquid volume aspirated from the measuring head (40).

26. Apparatus according to claim 1, characterized in that the measuring head (40) has a measuring point (104) which can be extended.

27. Apparatus according to claim 26, characterized in that the measuring point (104) is carried by a lever (108) which can be pivoted by an actuating rod (112) running in the lengthwise direction of the probe section (42) so that the measuring point (104) is moved with a radial movement component through a window (106) of the probe section (42).

28. Apparatus according to claim 27, characterized in that the actuating rod (112) is moved by a motor operator (114) whose driving force is adjustable (74).

29. Apparatus according to claim 26, characterized in that the measuring point is carried by a flexible transmission element (124) which is guided in a guide (126) in the probe housing (128) so that the transmission element (124) emerges with a radial direction component from the probe housing (128).

30. Apparatus according to claim 1, characterized in that the measuring head (40) comprises a light source (138), an optical system (130, 132) and an image converter (134).

31. Apparatus according to claim 1, characterized in that the measuring head (40) comprises a measuring light source (160), and at least one color filter (168) and a light detector (170).

32. Apparatus according claim 1, characterized in that the measuring device has a vibrator (144), a generator (146) operating on the vibrator, and means (148) for measuring the damping of the vibrator.

33. Apparatus according to claim 1, characterized in that the measuring device has a vibrator (144), an intermittently operating generator (146) operating on the vibrator (144) and a receiver (144) for vibrations reflected from the tissue, and means (88) for evaluating the intensity of the reflected vibrations.

34. Apparatus according to claim 1, characterized in that the measuring device has spaced electrodes (150, 152) which are connected to a resistance or impedance measuring unit (154) or represent part of a vibration circuit which is connected to a frequency measuring unit.

35. Apparatus according to claim 1, characterized in that the measuring device has a micro-porous test tube (156) or a hollow drill whose interior can be connected to a negative pressure source (80).

36. Apparatus according to claim 1, characterized in that the probe section (42) is cylindrical.

* * * * *